(12) United States Patent
DiBenedetto et al.

(10) Patent No.: US 7,506,460 B2
(45) Date of Patent: Mar. 24, 2009

(54) INTELLIGENT FOOTWEAR SYSTEMS

(75) Inventors: Christian DiBenedetto, North Plains, OR (US); Mark Arthur Oleson, Portland, OR (US); Charles Roth, Portland, OR (US); Mark Christopher Thompson, Portland, OR (US)

(73) Assignee: adidas International Marketing B.V., Amsterdam (NL)

( * ) Notice: Subject to any disclaimer, the term of this patent is extended or adjusted under 35 U.S.C. 154(b) by 0 days.

(21) Appl. No.: 11/522,727

(22) Filed: Sep. 18, 2006

(65) Prior Publication Data
US 2007/0011920 A1    Jan. 18, 2007

Related U.S. Application Data

(63) Continuation of application No. 10/385,300, filed on Mar. 10, 2003, now Pat. No. 7,188,439.

(51) Int. Cl.
*A43B 5/04* (2006.01)
(52) U.S. Cl. ............................. 36/132; 36/29; 36/1
(58) Field of Classification Search ............... 36/28, 36/29, 132, 136, 30 R, 25 R
See application file for complete search history.

(56) References Cited

U.S. PATENT DOCUMENTS

| | | | |
|---|---|---|---|
| 4,814,661 A | 3/1989 | Ratzlaff et al. | |
| 5,179,792 A | 1/1993 | Brantingham | |
| 5,269,081 A | 12/1993 | Gray | |
| 5,325,869 A | 7/1994 | Stokes | |
| 5,335,188 A | 8/1994 | Brisson | |
| 5,357,696 A | 10/1994 | Gray et al. | |
| 5,373,651 A | 12/1994 | Wood | |
| 5,383,290 A | 1/1995 | Grim | |
| 5,471,405 A | 11/1995 | Marsh | |
| 5,557,865 A | 9/1996 | Sjosvard | |
| 5,566,479 A | 10/1996 | Gray et al. | |
| 5,596,652 A | 1/1997 | Piatek et al. | |
| 5,598,849 A | 2/1997 | Browne | |
| 5,636,146 A | 6/1997 | Flentov et al. | |
| 5,720,200 A * | 2/1998 | Anderson et al. | ............. 73/172 |
| 5,724,667 A | 3/1998 | Hutchings | |
| 5,793,882 A | 8/1998 | Piatek et al. | |
| 5,794,361 A | 8/1998 | Sadler | |

(Continued)

FOREIGN PATENT DOCUMENTS

DE    1 013 126    8/1957

(Continued)

OTHER PUBLICATIONS

European Search Report for Application No. EP 04 00 5660, mailed from the European Patent Office on Oct. 7, 2004. (6 pgs.).

*Primary Examiner*—Ted Kavanaugh
(74) *Attorney, Agent, or Firm*—Goodwin Procter LLP

(57) ABSTRACT

The invention is directed to intelligent systems for articles of footwear that adjust automatically in response to a measured performance characteristic. The intelligent systems include one or more adjustable elements coupled to a mechanism that actuates the adjustable elements in response to a signal from a sensor to modify the performance characteristic of the article of footwear. The intelligent system adjusts the performance characteristics of the article of footwear without human intervention.

14 Claims, 26 Drawing Sheets

U.S. PATENT DOCUMENTS

| | | |
|---|---|---|
| 5,813,142 A | 9/1998 | Demon |
| 5,890,997 A | 4/1999 | Roth |
| 5,918,502 A | 7/1999 | Bishop |
| 5,929,332 A | 7/1999 | Brown |
| 5,931,763 A | 8/1999 | Alessandri |
| 5,937,462 A | 8/1999 | Huang |
| 5,955,667 A | 9/1999 | Fyfe |
| 5,960,380 A | 9/1999 | Flentov et al. |
| 6,013,007 A | 1/2000 | Root et al. |
| 6,018,705 A | 1/2000 | Gaudet et al. |
| 6,052,654 A | 4/2000 | Gaudet et al. |
| 6,077,193 A | 6/2000 | Buhler et al. |
| 6,122,340 A | 9/2000 | Darley et al. |
| 6,160,254 A | 12/2000 | Zimmerman et al. |
| 6,230,501 B1 | 5/2001 | Bailey, Sr. et al. |
| 6,266,623 B1 | 7/2001 | Vock et al. |
| 6,298,314 B1 | 10/2001 | Blackadar et al. |
| 6,336,365 B1 | 1/2002 | Blackadar et al. |
| 6,357,147 B1 | 3/2002 | Darley et al. |
| 6,375,612 B1 | 4/2002 | Guichon et al. |
| 6,396,413 B2 | 5/2002 | Hines et al. |
| 6,424,264 B1 | 7/2002 | Giraldin et al. |
| 6,430,843 B1 | 8/2002 | Potter et al. |
| 6,493,652 B1 | 12/2002 | Ohlenbusch et al. |
| 6,496,787 B1 | 12/2002 | Flentov et al. |
| 6,498,994 B2 | 12/2002 | Vock et al. |
| 6,499,000 B2 | 12/2002 | Flentov et al. |
| 6,516,284 B2 | 2/2003 | Flentov et al. |
| 6,526,158 B1 | 2/2003 | Goldberg |
| 6,531,963 B1 | 3/2003 | Nyfelt |
| 6,536,139 B2 | 3/2003 | Darley et al. |
| 6,539,336 B1 | 3/2003 | Vock et al. |
| 6,560,903 B1 | 5/2003 | Darley |
| 6,569,092 B1 | 5/2003 | Guichon et al. |
| 6,600,407 B2 | 7/2003 | Paek |
| 6,611,789 B1 | 8/2003 | Darley |
| 6,614,392 B2 | 9/2003 | Howard |
| 6,661,782 B1 | 12/2003 | Mustajarvi et al. |
| 6,807,753 B2 | 10/2004 | Steszyn et al. |
| 6,813,586 B1 | 11/2004 | Vock et al. |
| 6,825,777 B2 | 11/2004 | Vock et al. |
| 6,856,934 B2 | 2/2005 | Vock et al. |
| 6,865,825 B2 | 3/2005 | Bailey, Sr. et al. |
| 6,876,947 B1 | 4/2005 | Darley et al. |
| 6,882,955 B1 | 4/2005 | Ohlenbusch et al. |
| 6,885,971 B2 | 4/2005 | Vock et al. |
| 6,898,550 B1 | 5/2005 | Blackadar et al. |
| 6,959,259 B2 | 10/2005 | Vock et al. |
| 6,963,818 B2 | 11/2005 | Flentov et al. |
| 7,072,789 B2 | 7/2006 | Vock et al. |
| 7,092,846 B2 | 8/2006 | Vock et al. |
| 7,158,912 B2 | 1/2007 | Vock et al. |
| 7,162,392 B2 | 1/2007 | Vock et al. |
| 2001/0054014 A1 | 12/2001 | Noda et al. |
| 2002/0022551 A1 | 2/2002 | Watterson et al. |
| 2002/0077883 A1 | 6/2002 | Lancos et al. |
| 2002/0080198 A1 | 6/2002 | Giraldin et al. |
| 2002/0091796 A1 | 7/2002 | Higginson et al. |
| 2002/0142887 A1 | 10/2002 | O'Malley |
| 2002/0147629 A1 | 10/2002 | Alsafadi et al. |
| 2002/0147642 A1 | 10/2002 | Avallone et al. |
| 2002/0152645 A1 | 10/2002 | Darley et al. |
| 2002/0156677 A1 | 10/2002 | Peters et al. |
| 2002/0165758 A1 | 11/2002 | Hind et al. |
| 2002/0173407 A1 | 11/2002 | Bowman |
| 2002/0174025 A1 | 11/2002 | Hind et al. |
| 2003/0009308 A1 | 1/2003 | Kirtley |
| 2003/0009382 A1 | 1/2003 | D'Arbeloff et al. |
| 2003/0009913 A1 | 1/2003 | Potter et al. |
| 2003/0040922 A1 | 2/2003 | Bodin |
| 2003/0056401 A1 | 3/2003 | Kwon |
| 2003/0090386 A1 | 5/2003 | Giraldin et al. |
| 2003/0097878 A1 | 5/2003 | Farringdon et al. |
| 2003/0120353 A1 | 6/2003 | Christensen |
| 2003/0160732 A1 | 8/2003 | Van Heerden et al. |
| 2003/0163287 A1 | 8/2003 | Vock et al. |
| 2004/0064974 A1 | 4/2004 | Schuster |
| 2004/0177531 A1 | 9/2004 | DiBenedetto et al. |
| 2005/0080566 A1 | 4/2005 | Vock et al. |
| 2006/0014645 A1 | 1/2006 | Yavitz |
| 2006/0020421 A1 | 1/2006 | Darley et al. |
| 2006/0031039 A1 | 2/2006 | Flentov et al. |
| 2006/0052983 A1 | 3/2006 | Vock et al. |
| 2006/0235642 A1 | 10/2006 | Vock et al. |
| 2007/0006489 A1 | 1/2007 | Case, Jr. et al. |

FOREIGN PATENT DOCUMENTS

| | | |
|---|---|---|
| DE | 35 06 055 | 8/1986 |
| DE | 297 01 308 | 5/1997 |
| DE | 10201134 | 7/2003 |
| EP | 0472110 | 2/1992 |
| EP | 1457128 | 9/2004 |
| FR | 2 743 701 | 7/1997 |
| WO | WO 90/00866 | 2/1990 |
| WO | WO 94/05177 | 3/1994 |
| WO | WO-0033031 | 6/2000 |
| WO | WO 01/80678 | 11/2001 |

* cited by examiner

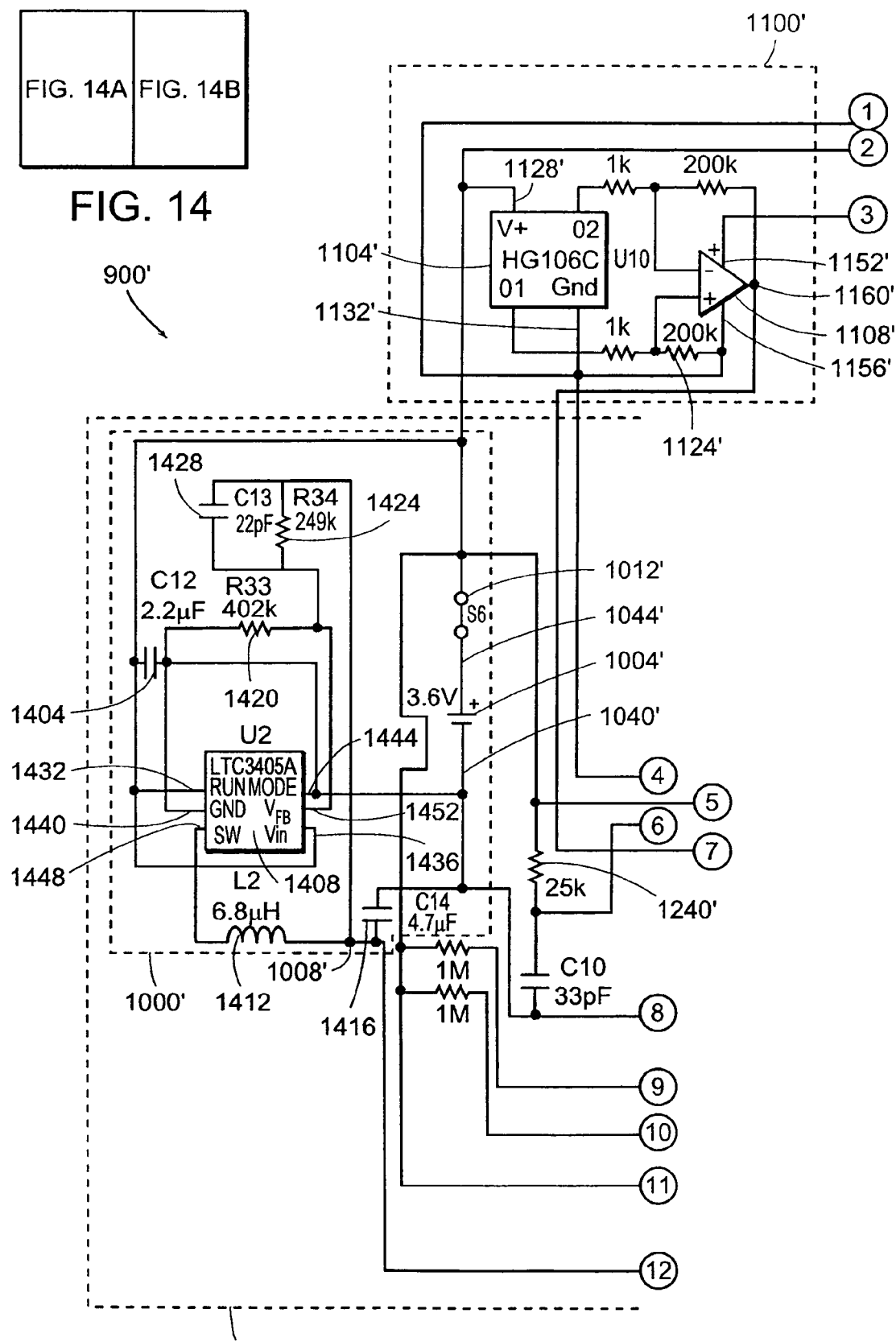

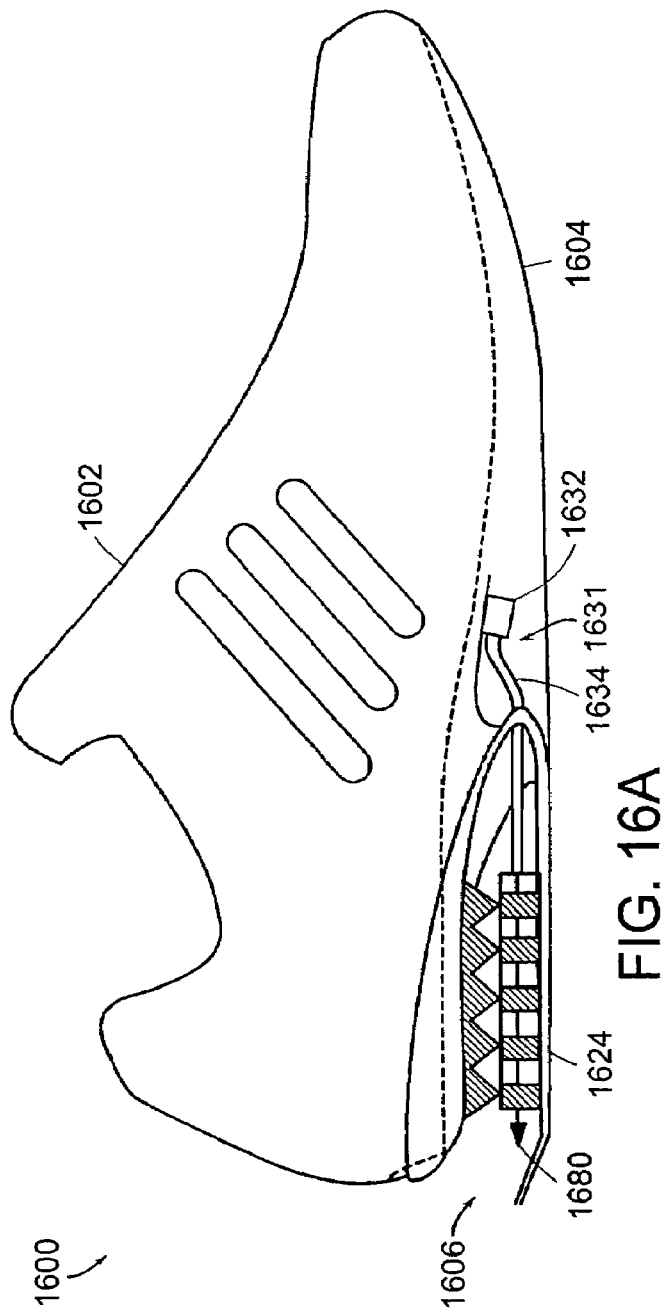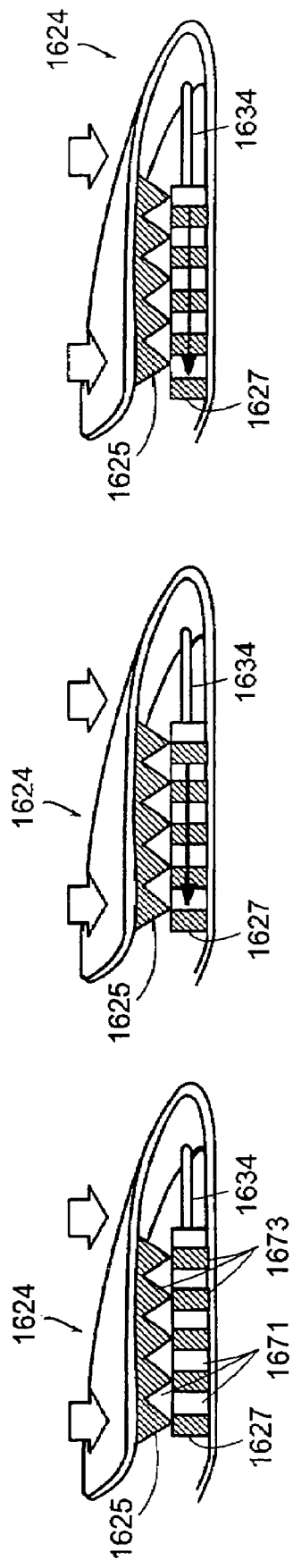
FIG. 16A
FIG. 16B
FIG. 16C
FIG. 16D

INTELLIGENT FOOTWEAR SYSTEMS

CROSS REFERENCE TO RELATED APPLICATION

This application is a continuation of, claims priority to and the benefit of, and incorporates herein by reference in its entirety U.S. patent application Ser. No. 10/385,300, which was filed on Mar. 10, 2003.

TECHNICAL FIELD

The invention generally relates to intelligent systems for articles of footwear. In particular, the invention relates to automatic, self-adjusting systems that modify a performance characteristic of the article of footwear.

BACKGROUND INFORMATION

Conventional athletic shoes include an upper and a sole. The sole is usually manufactured of a material chosen to attempt to optimize a particular performance characteristic of the shoe, for example, stability or stiffness. Typically, the sole includes a midsole and an outsole, either of which can include, a resilient material to protect a wearer's foot and leg. One drawback with conventional shoes is that performance characteristics, such as cushioning and stiffness, are not adjustable. The wearer must, therefore, select a specific shoe for a specific activity. For example, for activities requiring greater cushioning, such as running, the wearer must select one type of shoe and for activities requiring greater stiffness for support during lateral movement, such as basketball, the wearer must select a different type of shoe.

Some shoes have been designed to allow for adjustment in the degree of cushioning or stiffness provided by the sole. Many of these shoes employ a fluid bladder that can be inflated or deflated as desired. A disadvantage presented by these shoes is that one or more of the bladders can fail, rendering the cushioning system effectively useless. Moreover, many of the shoes employing fluid bladders do not allow for small-scale changes to the degree of cushioning provided by the sole. Often, the change to the degree of cushioning provided by the sole in pressurizing or depressurizing, or in partially pressurizing or partially depressurizing, a bladder will typically be larger than that desired by the wearer. In other words, bladders are typically not capable of fine adjustments.

A further disadvantage of many of the shoes designed to allow for adjustment in the degree of cushioning or stiffness provided by the sole is that they are only manually adjustable. Accordingly, in order to adjust such shoes the wearer is required to interrupt the specific activity in which he/she is engaged. With some shoes, the wearer may also be required to partially disassemble the shoe, re-assemble the shoe, and even exchange shoe parts. Moreover, the wearer, to his or her dissatisfaction, may be limited in the amount of adjustment that can be made.

Some shoes have been designed to automatically adjust the degree of cushioning or stiffness provided by the sole. These shoes measure the amount of force or pressure exerted on the sole by the wearer's foot when the wearer's foot strikes the ground. Through analysis and investigation, it has been discovered that the mere measurement of force or pressure alone, however, is too limited, as it provides no information relating to the performance of the shoe. For example, measuring force provides no indication as to whether the sole has either over-compressed or under-compressed for that particular wearer without prior investigation into the normal forces exerted by the wearer during the activity. If the sole is either over-compressed or under-compressed, the shoe is poorly matched to the wearer's activity and needs. In essence, the wearer's body has to adapt to the shoe. The biomechanical needs of the wearer are poorly met, if at all.

In sum, shoes that have been designed to allow for some adjustment in the degree of cushioning or stiffness provided by the sole still fall short of accommodating the wearer's needs. Specifically, they are not fully adjustable throughout the range of the biomechanical needs of the particular wearer or lack the ability to sense the true needs of the wearer. As a result, the wearer must still, in some way, adapt his or her body to the environment presented by the shoe.

There is, therefore, a need for a shoe that senses the biomechanical needs of the wearer, automatically adjusts a performance characteristic of the shoe to accommodate the biomechanical needs of the wearer, for example the degree of cushioning or stiffness provided by the sole, and avoids the drawbacks of bladder cushioning or manually adjustable shoes.

SUMMARY OF THE INVENTION

The invention is directed to intelligent systems for articles of footwear that adjust a feature of the footwear in response to the footwear's environment, without human interaction. In other words, the footwear is adaptive. For example, the intelligent system can continuously sense the biomechanical needs of the wearer and concomitantly modify the footwear to an optimal configuration. The intelligent system includes a sensing system, a control system, and an actuation system.

The sensing system measures a performance characteristic of the article of footwear and sends a signal to the control system. The signal is representative of the measured performance characteristic. The control system processes the signal to determine if, for example, the performance characteristic deviates from an acceptable range or exceeds a predetermined threshold. The control system sends a signal to the actuation system relative to the deviation. The actuation system modifies a feature of the footwear in order to obtain an optimal performance characteristic.

In one aspect, the invention relates to an intelligent system for an article of footwear. The system includes a control system, a power source electrically coupled to the control system, an adjustable element, and a driver coupled to the adjustable element. The driver adjusts the adjustable element in response to a signal from the control system.

In another aspect, the invention relates to an article of footwear including an upper coupled to a sole and an intelligent system at least partially disposed in the sole. The system includes a control system, a power source electrically coupled to the control system, an adjustable element, and a driver coupled to the adjustable element. The driver adjusts the adjustable element in response to a signal from the control system.

In various embodiments of the foregoing aspects, the system modifies a performance characteristic of the article of footwear, such as compressibility, resiliency, compliancy, elasticity, damping, energy storage, cushioning, stability, comfort, velocity, acceleration, jerk, stiffness, or combinations thereof. In one embodiment, the adjustable element is adjusted by at least one of translation, rotation, reorientation, modification of a range of motion, or combinations thereof. The system may include a limiter for limiting a range of motion of the adjustable element. The control system includes a sensor and electrical circuitry. The sensor may be a pressure sensor, a force transducer, a hall effect sensor, a strain gauge, a piezoelectric element, a load cell, a proximity sensor, an optical sensor, an accelerometer, a hall element or sensor, a capacitance sensor, an inductance sensor, an ultrasonic transducer and receiver, a radio frequency emitter and receiver, a magneto-resistive element, or a giant magneto-resistive element. In various embodiments, the driver may be a worm drive, a lead screw, a rotary actuator, a linear actuator, a gear train, a linkage, or combinations thereof.

In still other embodiments, the adjustable element may be at least partially disposed in at least one of a forefoot portion, a midfoot portion, and a rearfoot portion of the article of footwear. In one embodiment, the article of footwear has a sole including an outsole and a midsole and the adjustable element is disposed at least partially in the midsole. In various embodiments, the adjustable element may be generally longitudinally disposed within the article of footwear, or the adjustable element may be generally laterally disposed within the article of footwear, or both. For example, the adjustable element may extend from a heel region to an arch region of the article of footwear or from an arch region to a forefoot region of the article of footwear or from a forefoot region to a heel region of the article of footwear. Furthermore, the adjustable element may be at least partially disposed in a lateral side, or a medial side, or both of the article of footwear.

In another aspect, the invention relates to a method of modifying a performance characteristic of an article of footwear during use. The method includes the steps of monitoring the performance characteristic of the article of footwear, generating a corrective driver signal, and adjusting an adjustable element based on the driver signal to modify the performance characteristic of the article of footwear. In one embodiment, the steps are repeated until a threshold value of the performance characteristic is obtained.

In various embodiments of the foregoing aspect, the generating step includes the substeps of comparing the monitored performance characteristic to a desired performance characteristic to generate a deviation and outputting a corrective driver signal magnitude based on the deviation. In one embodiment, the corrective driver signal has a predetermined magnitude. Further, the monitoring step may include the substeps of measuring a magnetic field of a magnet with a proximity sensor, wherein at least one of the magnet and the sensor are at least partially disposed within the sole and are vertically spaced apart in an unloaded state, and comparing the magnetic field measurement during compression to a threshold value. In one embodiment, the monitoring step involves taking multiple measurements of the magnetic field during compression and comparing an average magnetic field measurement to the threshold value.

In additional embodiments, the method may include the step of limiting a range of motion of the adjustable element with a limiter and the adjusting step may include adjusting the limiter a predetermined distance. The adjustment step may be performed when the article of footwear is in an unloaded state. In one embodiment, the adjustment step is terminated when a threshold value of the performance characteristic is reached.

In various embodiments of all of the foregoing aspects of the invention, the adjustable element may be an expansion element, a multiple density foam, a skeletal element, a multidensity plate, or combinations thereof. The adjustable element may exhibit an anisotropic property. In one embodiment, the adjustable element may be a generally elliptically-shaped expansion element. Further, the system may include a manual adjustment for altering or biasing the performance characteristic of the adjustable element, or an indicator, or both. The manual adjustment may also alter a threshold value of the performance characteristic. The indicator may be audible, visual, or both. For example, the indicator may be a series of light-emitting diodes.

In another aspect, the invention relates to a system for measuring compression within an article of footwear. The system includes a sensor at least partially disposed within a sole of the article of footwear and a magnet generally aligned with and spaced from the sensor. The sensor may be a hall effect sensor, a proximity sensor, a hall element or sensor, a capacitance sensor, an inductance sensor, an ultrasonic transducer and receiver, a radio frequency emitter and receiver, a magneto-resistive element, or a giant magneto-resistive element. The system may include a processor. In one embodiment, the sensor measures a magnetic field generated by the magnet and the processor converts the magnetic field measurement into a distance measurement representing an amount of compression of the sole in correlation with respective time measurements. The processor may convert the distance measurements into a jerk value.

In various embodiments of the foregoing aspect, the system further includes a driver coupled to the sensor and an adjustable element coupled to the driver. The system may include a limiter for limiting a range of motion of the adjustable element. In one embodiment, a performance characteristic of the article of footwear is modified in response to a signal from the sensor. In one embodiment, the signal corresponds to an amount of compression of the sole.

In another aspect, the invention relates to a method of providing comfort in an article of footwear. The method includes the steps of providing an adjustable article of footwear and determining a jerk value. The method may further include the step of modifying a performance characteristic of the adjustable article of footwear based on the jerk value.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 16A is a schematic side view of an article of footwear including yet another alternative embodiment of an intelligent system in accordance with the invention;

FIGS. 16B-16D are schematic side views of the intelligent system of FIG. 16A in various orientations;

DESCRIPTION

Embodiments of the present invention are described below. It is, however, expressly noted that the present invention is not limited to these embodiments, but rather the intention is that modifications that are apparent to the person skilled in the art are also included. In particular, the present invention is not intended to be limited to any particular performance characteristic or sensor type or arrangement. Further, only a left or right shoe is depicted in any given figure; however, it is to be understood that the left and right shoes are typically mirror images of each other and the description applies to both left and right shoes. In certain activities that require different left and right shoe configurations or performance characteristics, the shoes need not be mirror images of each other.

Figure 1:
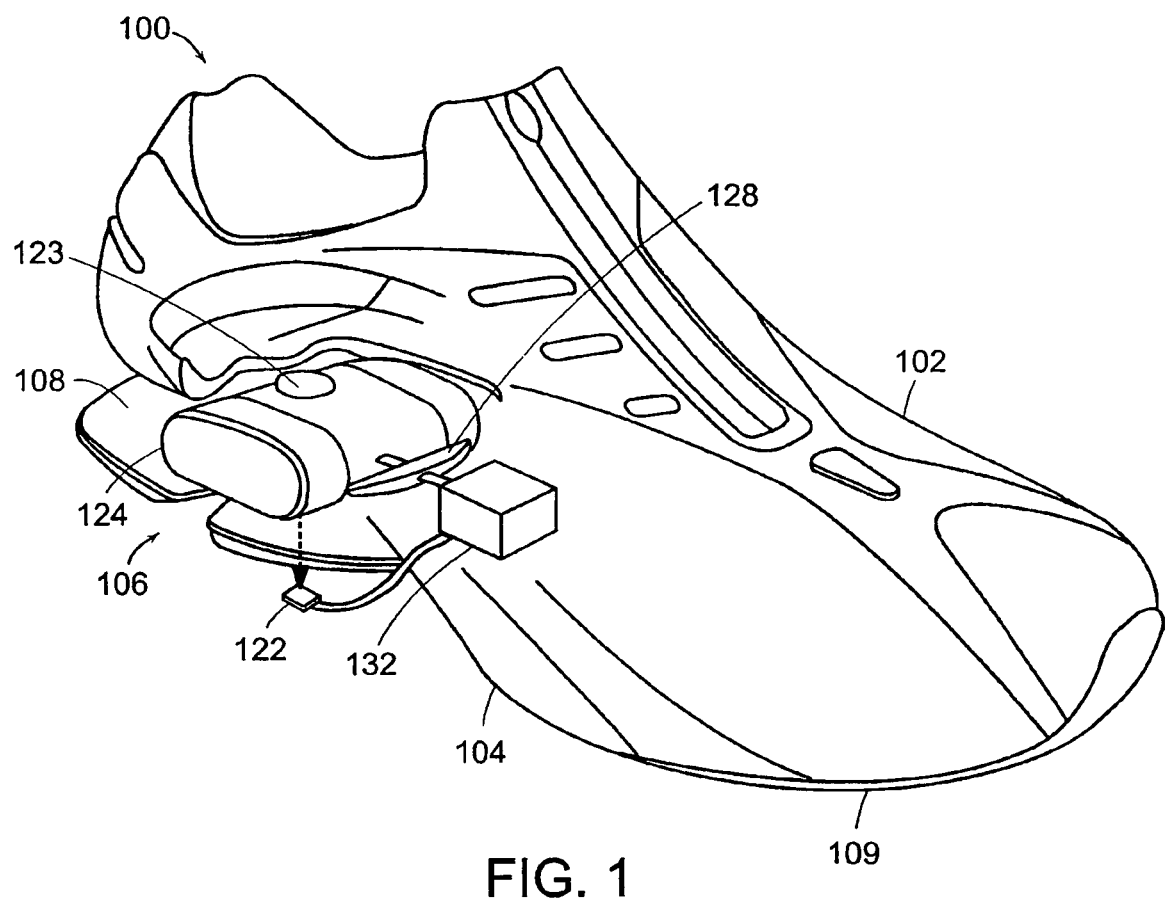
FIG. 1 is a partially exploded schematic perspective view of an article of footwear including an intelligent system in accordance with one embodiment of the invention.

FIG. 1 depicts an article of footwear 100 including an upper 102, a sole 104, and an intelligent system 106. The intelligent system 106 is laterally disposed in a rearfoot portion 108 of the article of footwear 100. The intelligent system 106 could be disposed anywhere along the length of the sole 104 and in essentially any orientation. In one embodiment, the intelligent system 106 is used to modify the compressibility of a heel area of the article of footwear 100. In another embodiment, the intelligent system 106 can be located in a forefoot portion 109 and can be moved into and out of alignment with a flex line or otherwise configured to vary a push-off characteristic of the footwear 100. In yet another embodiment, the footwear 100 could include multiple intelligent systems 106 disposed in multiple areas of the footwear 100. The intelligent system 106 is a self-adjusting system that modifies one or more performance characteristics of the article of footwear 100. The operation of the intelligent system 106 is described in detail hereinbelow.

Figure 2A:
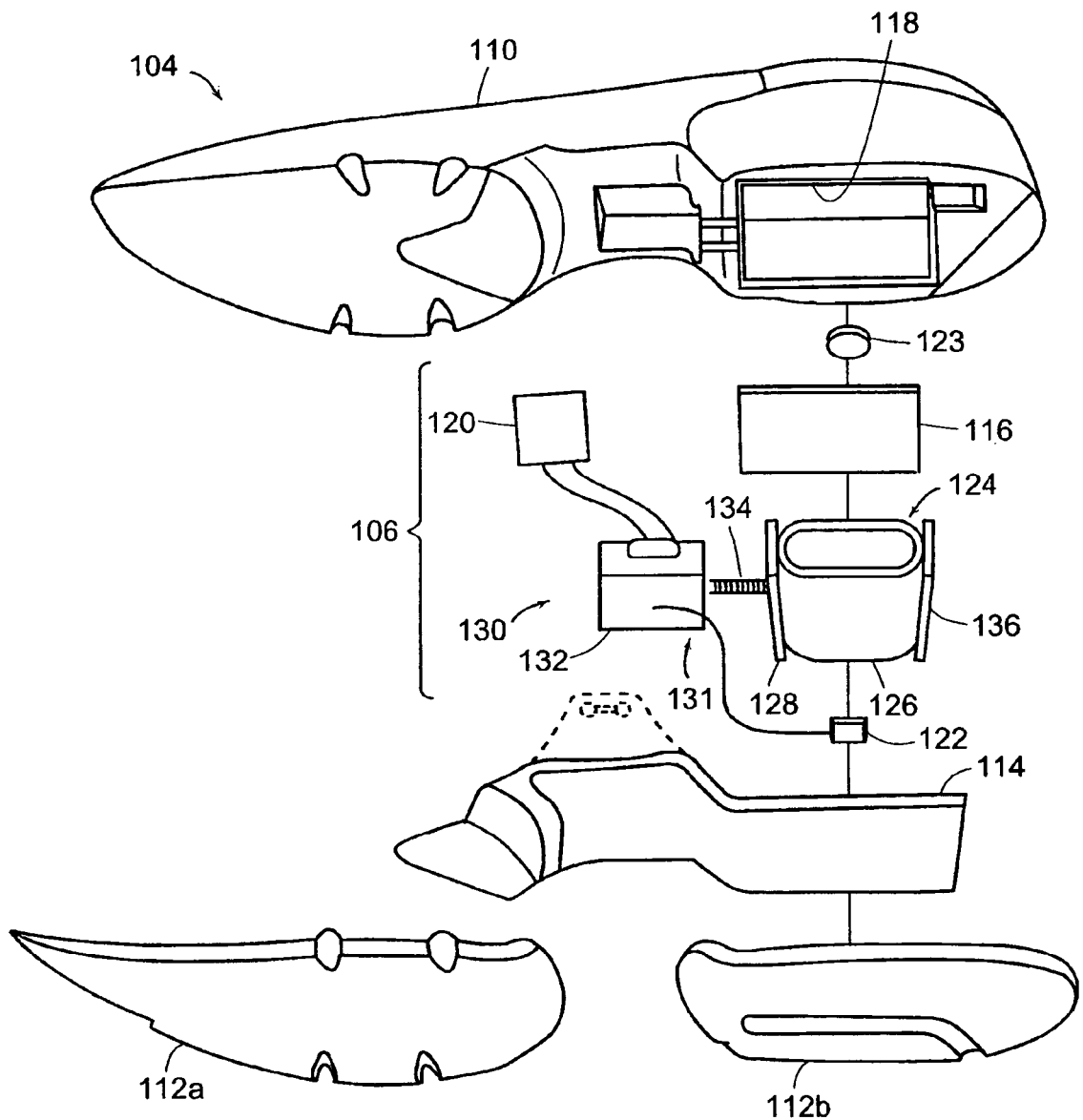
FIG. 2A is an exploded schematic perspective view of the sole of the article of footwear of FIG. 1.

FIG. 2A depicts an exploded view of a portion of the sole 104 of FIG. 1. The sole 104 includes a midsole 110, an outsole 112a, 112b, an optional lower support plate 114, an optional upper support plate 116, and the intelligent system 106. The upper and lower support plates may, among other purposes, be included to help constrain the intelligent system 106 in a particular orientation. The intelligent system 106 is disposed within a cavity 118 formed in the midsole 110. In one embodiment, the midsole 110 is a modified conventional midsole and has a thickness of about 10 mm to about 30 mm, preferably about 20 mm in the heel portion. The intelligent system 106 includes a control system 120 and an actuation system 130 in electrical communication therewith, both of which are described in greater detail hereinbelow. The actuation system 130 includes a driver 131 and an adjustable element 124. The control system 120 includes a sensor 122, for example a proximity sensor, a magnet 123, and electrical circuitry (see FIGS. 9-14). In the embodiment shown, the sensor 122 is disposed below the adjustable element 124 and the magnet 123 is vertically spaced from the sensor 122. In this particular embodiment, the magnet 123 is disposed above the adjustable element 124 and is a Neodymium Iron Bore type magnet. The actual position and spacing of the sensor 122 and magnet 123 will vary to suit a particular application, for example, measuring and modifying the compressibility of the sole. In this particular embodiment, the sensor 122 and magnet 123 are located in a spot that corresponds generally to where maximum compression occurs in the rearfoot portion 108 of the footwear 100. Typically, the spot is under the wearer's calcaneous. In such an embodiment, the sensor 122 and magnet 123 are generally centered between a lateral side and a medial side of the sole 104 and are between about 25 mm and about 45 mm forward of a posterior aspect of the wearer's foot.

Figure 2B:
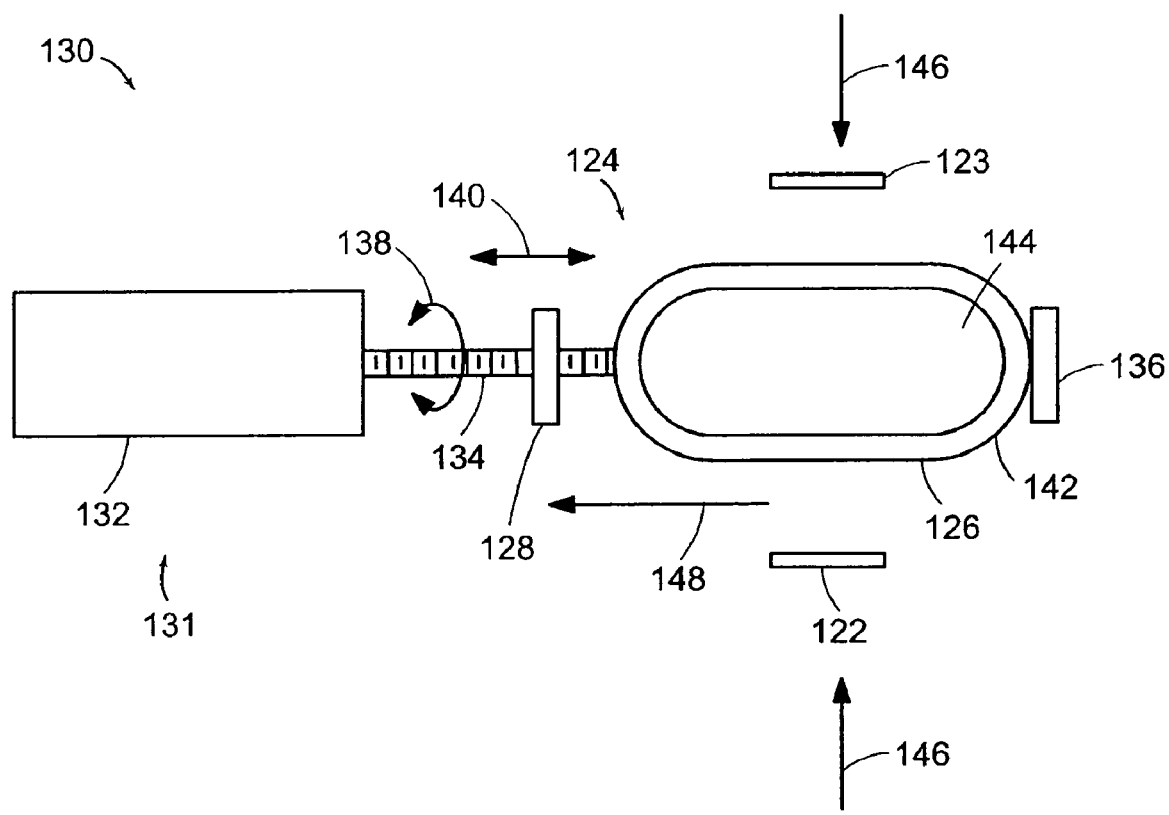
FIG. 2B is an enlarged schematic side view of the intelligent system of FIG. 2A illustrating the operation of the adjustable element.

FIG. 2B depicts a portion of the intelligent system 106, in particular the actuation system 130, in greater detail. The intelligent system 106 is preferably encased in a sealed, waterproof enclosure. The actuation system 130 generally includes a driver 131, which includes a motor 132 and a transmission element 134, and an adjustable element 124, which includes a limiter 128, an expansion element 126, and a stop 136. The embodiment of the particular driver 131 shown is a lead screw drive, made up of a bi-directional electric motor 132 and a threaded rod that forms the transmission element 134. In one embodiment, the motor 132 can be a radio-controlled servomotor of the type used in model airplanes. The threaded rod could be made of steel, stainless steel, or other suitable material.

The motor 132 is mechanically coupled to the transmission element 134 and drives the element 134 in either a clockwise or counter-clockwise direction as indicated by arrow 138. The transmission element 134 threadedly engages the limiter 128 and transversely positions the limiter 128 relative to the expansion element 126, as shown generally by arrow 140. Because the limiter 128 is threadedly engaged with the transmission element 134 and prevented from rotation relative to the motor 132 and the footwear 100, no power is required to maintain the limiter's position. There is sufficient friction in the actuation system 130 and a sufficiently fine thread on the transmission element 134 to prevent inadvertent rotation of the element 134 during a heel strike. In one example, the limiter 128 advances toward the expansion element 126 when the motor 132 drives the transmission element 134 in the clockwise direction and the limiter 128 moves away from the expansion element 126 when the motor 132 drives the transmission element 134 in the counter-clockwise direction. Alternatively, other types of drivers are possible. For example, the driver 131 could be essentially any type of rotary or linear actuator, a gear train, a linkage, or combinations thereof.

The expansion element 126 is generally cylindrical, with an elongated circular or elongated generally elliptically-shaped cross-section. The arcuate ends of the expansion elements are not necessarily semi-circular in shape. The radius of the arcuate ends will vary to suit a particular application and can be varied to control the amount of longitudinal expansion of the expansion element 126 when under compressive loading vertically. In general, the larger the radius of the arcuate end, the greater longitudinal expansion is possible under vertical compression loading. The expansion element 126 has a solid outer wall 142 and a optional compressible core 144 of foam or other resilient material. The size, shape, and materials used in the expansion element 126 will be selected to suit a particular application. In the embodiment shown, the transmission element 134 extends through the expansion element 126 and connects to a stop 136. The stop 136 prevents movement of the expansion element 126 in a direction away from the limiter 128. Alternatively, the stop 136 could be a rear wall of the cavity 118.

The general operation of the adjustable element 124 is described with respect to an application where the intelligent system 106 is used to modify cushioning in the article of footwear 100 in response to a measured parameter, for example compression of the midsole 110. The expansion element 126 is allowed to compress when acted on by a vertical force, depicted generally by arrows 146. The expansion element 126 expands in the horizontal direction (arrow 148) when compressed. The limiter 128 is used to control this movement. As the horizontal movement is limited, the vertical movement is limited as well. The expansion element 126 has a bi-modal compression response, which is discussed in greater detail below with respect to FIG. 18.

The intelligent system 106 can control the amount of compression a user creates in the article of footwear 100. As an example, when a user wearing the article of footwear 100 engages a ground surface during a stride, the vertical force 146 is applied to the expansion element 126 via the sole 104. The force 146 causes the expansion element 126 to expand during ground contact until it contacts the limiter 128, thereby controlling the compression of the sole 104.

During compression, the sensing portion of the control system 120 measures field strength of the magnet 123. In the embodiment shown, the sensor 122 is disposed proximate the bottom of the midsole 110 and the magnet 123 is disposed proximate the top of the midsole 110. The magnetic field strength detected by the sensor 122 changes as the magnet 123 moves closer to the sensor 122, as the midsole 110 is compressed. The system can be calibrated, such that this magnetic field strength can be converted to a distance. It is the change in distance that indicates how much the midsole 110 has been compressed. The control system 120 outputs a signal to the actuation system 130 based on the change in distance or compression measurement.

The actuation system 130 then modifies the hardness or compressibility of the midsole 110 based on the signal received from the control system 120. The actuation system 130 utilizes the transmission element 134 as the main moving component. The operation of the intelligent system 106 is described in greater detail below, with respect to the algorithm depicted in FIG. 8.

Figure 3:
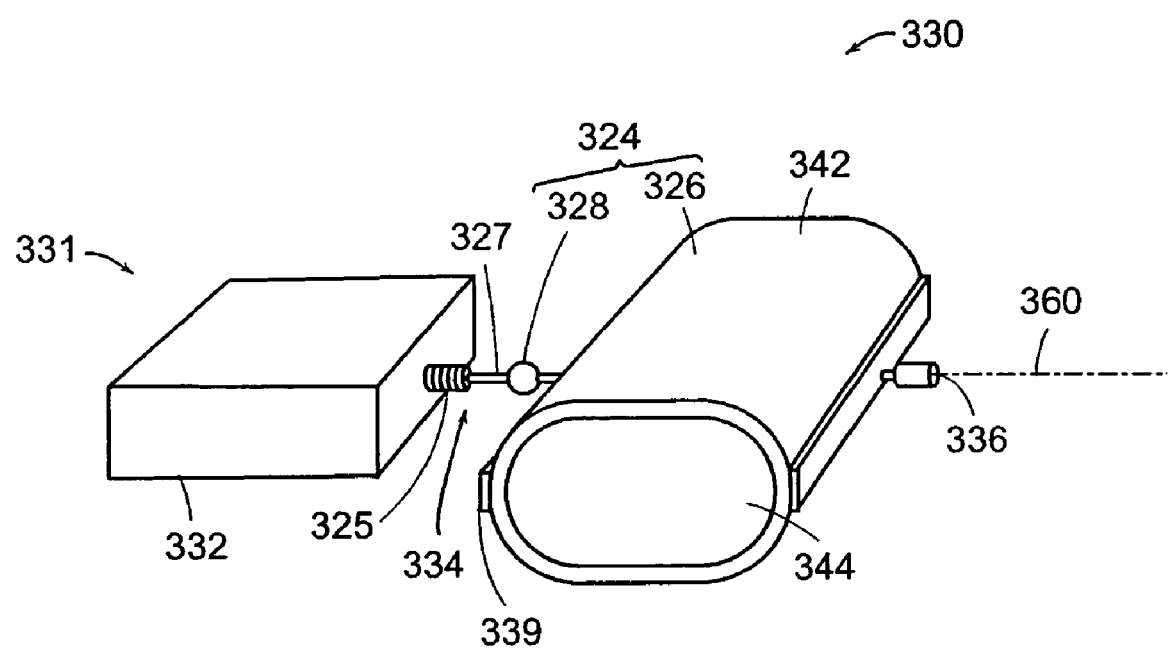
FIG. 3 is a schematic perspective view of an alternative embodiment of an adjustable element in accordance with the invention.

FIG. 3 depicts a portion of an alternative embodiment of an intelligent system 306 in accordance with the invention, in particular the actuation system 330. The actuation system 330 includes a driver 331 and an adjustable element 324. The adjustable element 324 includes an expansion element 326 and limiter 328 similar to that described with respect to FIG. 2B. The driver 331 includes a motor 332 and a transmission element 334, in this embodiment a hollow lead screw 325 through which a cable 327 passes. The cable 327 runs through the expansion element 326 and has a stop 336 crimped to one end. The limiter 328 is a generally cylindrically-shaped element that is slidably disposed about the cable 327 and acts as a bearing surface between the screw 325 and the expansion element 326, in particular a bearing arm 339 coupled to the expansion element 326. A similar bearing arm is disposed proximate the stop 336, to distribute loads along the depth of the expansion element 326. In one embodiment, the motor 332 is a 6 mm pager motor with a 300:1 gear reduction. The cable 327, screw 325, limiter 328, and bearing arm 339 may be made of a polymer, steel, stainless steel, or other suitable material. In one embodiment, the cable 327 is made from stainless steel coated with a friction-reducing material such as that sold by DuPont under the trademark Teflon®.

In operation, the cable 327 is fixedly attached to the driver 331 and has a fixed length. The cable 327 runs through the screw 325, which determines the amount of longitudinal travel of the expansion element 326 that is possible. For example, as a vertical force is applied to the expansion element 326, the element 326 expands longitudinally along the cable 327 until it hits the limiter 328, which is disposed between the expansion element 326 and the end of the screw 325. The motor 332 rotates the screw 325 to vary the length of the cable 327 that the limiter 328 can slide along before contacting the screw 325 and expansion element 326. The screw 325 moves a predetermined distance either towards or away from the element 326 in response to the signal from the control system. In one embodiment, the screw 325 may travel between about 0 mm to about 20 mm, preferably about 0 mm to about 10 mm.

In an alternative embodiment, the adjustable element 324 includes two motors 332 and cables 327 oriented substantially parallel to one another. Two cables 327 aid in holding the expansion element 326 square relative to a longitudinal axis 360 of the adjustable element 324 depicted in FIG. 3. In addition, other types of expansion element/limiter arrangements are possible. For example, a circumferential or belly band type limiter may be used instead of a diametral or longitudinal type limiter. In operation, the driver 331 varies the circumference of the belly band to vary the range of expansion of the element 326, the larger the circumference, the larger the range of expansion. Other possible arrangements include shape memory alloys and magnetic rheological fluid.

Figure 4A:
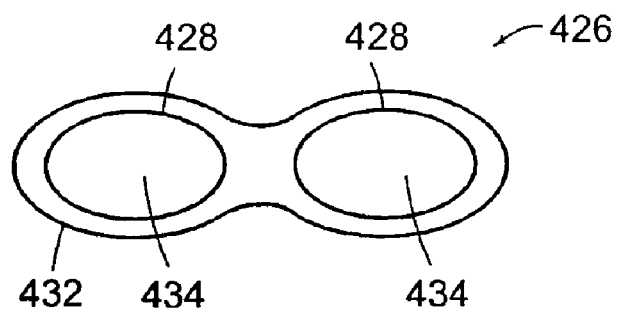
FIGS. 4A-4E are schematic side views of alternative embodiments of an adjustable element in accordance with the invention.
Figure 4B:
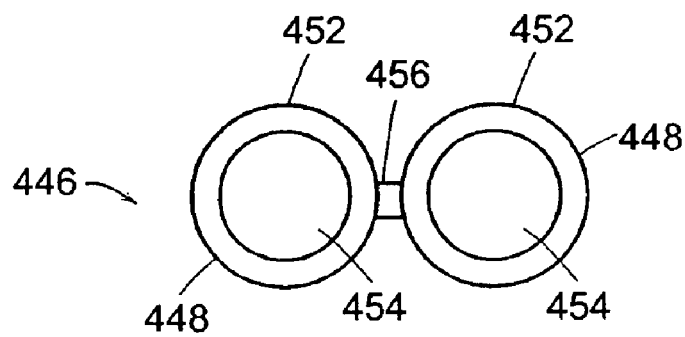
Figure 4C:
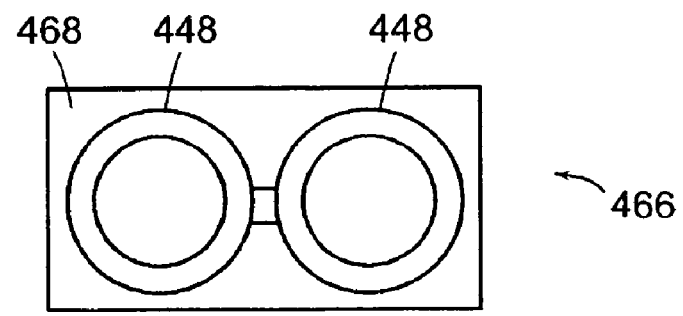
Figure 4D:
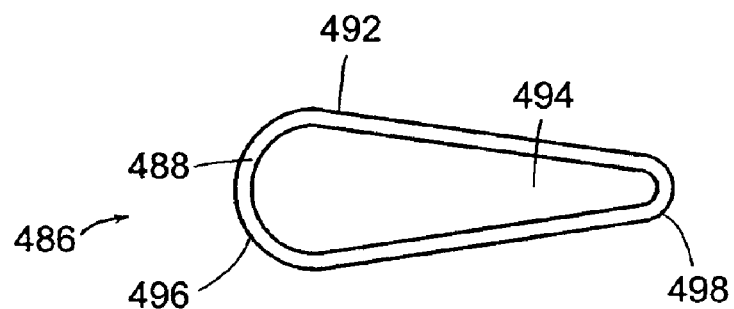

FIGS. 4A-4E depict alternative adjustable elements, with each shown in an unloaded state. In particular, FIGS. 4A-4D depict certain different possible shapes for the expansion element. In FIG. 4A, the expansion element 426 includes two cylinders 428 having generally elliptically-shaped cross-sections and formed as a single element. Alternatively, the cylinder cross-sectional shape could be any combination of linear and arcuate shapes, for example, hexagonal or semicircular. The cylinders 428 include a wall 432 and a pair of cores 434 that may be hollow or filled with a foam or other material. FIG. 4B depicts an expansion element 446 having two separate cylinders 448 having generally circular cross-sections and coupled together. The cylinders 448 each have a wall 452 and a core 454. FIG. 4C depicts an expansion element 466 including two cylinders 448 as previously described. In FIG. 4C, the expansion element 466 includes a foam block 468 surrounding the cylinders 448. The foam block 468 may replace the core or be additional to the core. FIG. 4D depicts yet another embodiment of an expansion element 486. The expansion element 486 includes a cylinder 488 having an elongate sector cross-sectional shape. The cylinder includes a wall 492 and a core 494. The cylinder 488 includes a first arcuate end 496 and a second arcuate end 498. The first arcuate end 496 has a substantially larger radius than the second arcuate end 498, thereby resulting in greater horizontal displacement at the first arcuate end when under load. Additionally, the wall thickness of any cylinder can be varied and/or the cylinder could be tapered along its length. In embodiments of the expansion element 126 that use a foam core, it is undesirable to bond the foam core to the walls of the expansion element 126. Bonding the foam to the walls may inhibit horizontal expansion.

Figure 4E:
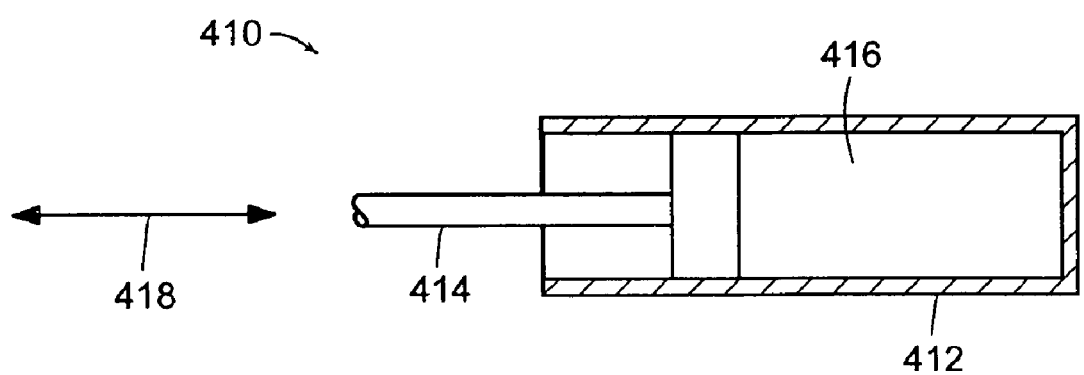

FIG. 4E depicts an alternative type of adjustable element 410. The adjustable element 410 includes a relatively flexible structural cylinder 412 and piston 414 arrangement. The internal volume 416 of the cylinder 412 varies as the piston 414 moves into and out of the cylinder 412, shown generally by arrow 418. The piston 414 is moved linearly by the driver 131 in response to the signal from the control system 120. By varying the volume 416, the compressibility of the cylinder 412 is varied. For example, when the piston 414 is moved into the cylinder 412, the volume is reduced and the pressure within the cylinder is increased; the greater the pressure, the harder the cylinder. While this system may appear similar to that of an inflatable bladder, there are differences. For example, in this system, the amount of fluid, e.g., air, stays constant, while the volume 416 is adjusted. Further, bladders primarily react based on the pressure within the bladder, whereas the element 410 depicted in FIG. 4E uses the structure of the cylinder in combination with the internal pressure. The two are fundamentally different in operation. For example, the inflatable bladder, like a balloon, merely holds the air in and provides no structural support, while the cylinder, like a tire, uses the air to hold up the structure (e.g. the tire sidewalls). In addition, the piston 414 and driver 131 arrangement allows for fine adjustment of the pressure and compressibility of the adjustable element 410.

Figure 5A:
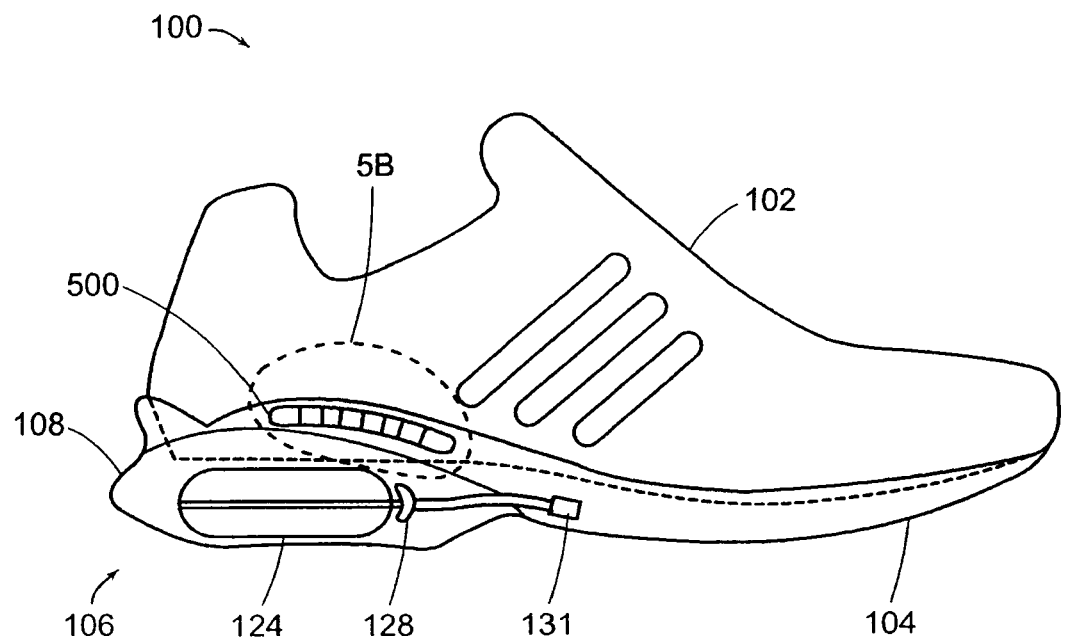
FIG. 5A is a schematic side view of the article of footwear of FIG. 1 showing select internal components.

FIG. 5A depicts a side view of the article of footwear 100 of FIG. 1. The intelligent system 106 is disposed generally in the rearfoot portion 108 of the article of footwear 100. As shown in FIG. 5A, the intelligent system 106 includes the adjustable element 124 with the limiter 128 and the driver 131. Also shown is a user-input module 500 (FIG. 5B) including user-input buttons 502, 504 and an indicator 506. The user can set the compression range or other performance characteristic target value of the article of footwear 100, by pushing input button 502 to increase the target value or pushing input button 504 to decrease the target value or range. In an alternative embodiment, the user-input module 500 can be remotely located from the shoe. For example, a wristwatch, personal digital assistant (PDA), or other external processor could be used alone or in combination with the user-input module 500 disposed on the article of footwear, to allow the user to customize characteristics of the intelligent system 106. For example, the user may press buttons on the wristwatch to adjust different characteristics of the system 106. In addition, the system 106 may include an on and off switch.

Figure 5B:
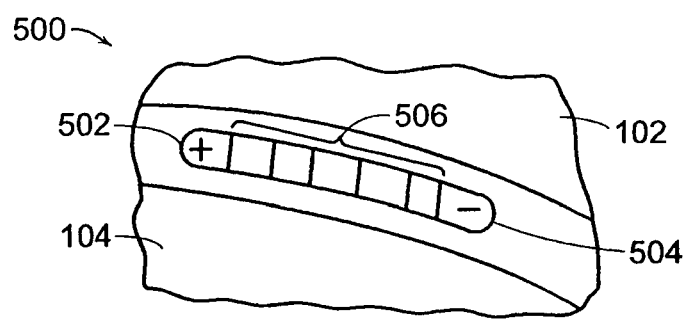
FIG. 5B is an enlarged schematic view of a portion of the article of footwear of FIG. 5A.

The user-input module 506 is shown in greater detail in FIG. 5B. The indicator(s) 506 may be one or more light emitting diodes (LEDs) or organic light emitting diodes (OLE's), for example. In the embodiment shown, the indicator 506 is a series of LEDs printed on a flex-circuit that glow to indicate the range of compression selected; however, the indicators could also indicate the level of hardness of the midsole or some other information related to a performance characteristic of the footwear 100. Alternatively or additionally, the indicator may be audible.

Figure 6:
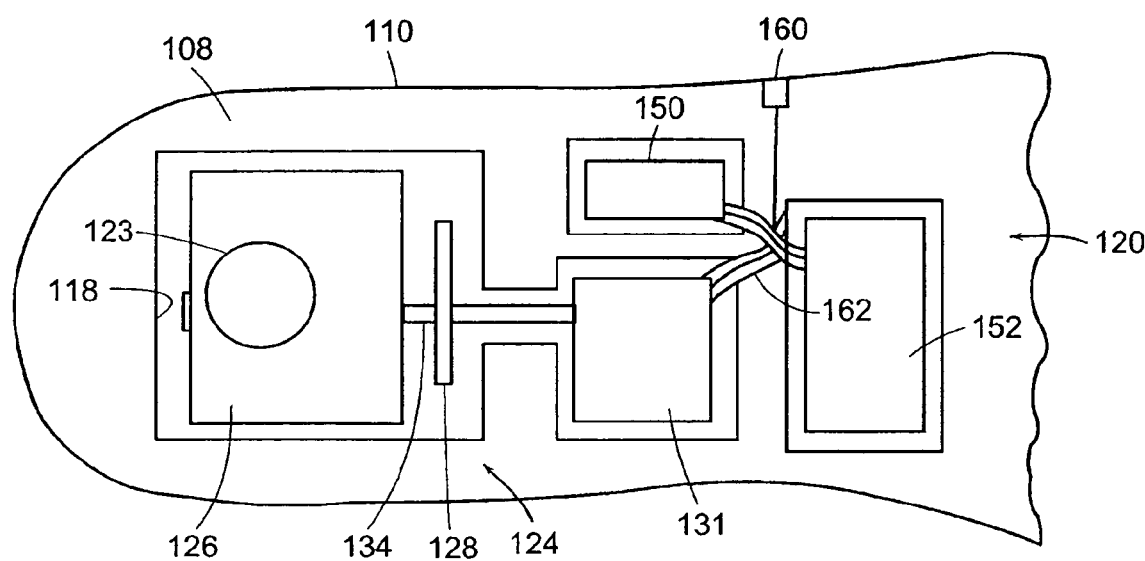
FIG. 6 is a schematic top view of a portion of the sole of FIG. 2A with a portion of the sole removed to illustrate the layout of select internal components of the intelligent system.

FIG. 6 depicts a top view of one possible arrangement of select components of the intelligent system of FIG. 1. The adjustable element 124 is disposed in the rearfoot portion 108 of the midsole 110 with the expansion element 126 laterally disposed within the cavity 118. The driver 131 is disposed adjacent to the expansion element 126. Adjacent to the driver 131 is the control system 120. The control system 120 includes a control board 152 that holds two micro-controllers, one for controlling the driver 131 and one for processing the algorithm. Further, the system 106 includes a power source 150, for example a 3.6V ½ AA battery. The power source 150 supplies power to the driver 131 and the control system 120 via wires 162 or other electrical connection, such as a flex-circuit.

The system 106 further includes the magnet 123 and the aligned sensor 122 (not shown), which is located under the expansion element 126 and is electrically coupled to the control system 120. The magnet 123 is located above the expansion element 126, but below an insole and/or sock liner. Further, the entire intelligent system 106 can be built into a plastic casing to make the system 106 waterproof. In addition, the system 106 can be built as a single module to facilitate fabrication of the sole 104 and may be pre-assembled to the lower support plate 114 (not shown in FIG. 6). In one embodiment, the system 106 is removable, thereby making the system 106 replaceable. For example, the outsole 112a, 112b may be configured (e.g., hinged) to allow the system to be removed from the cavity 118 of the midsole 110.

The system 106 may also include an interface port 160 that can be used to download data from the intelligent system 106, for example to a PDA or other external processor. The port 106 can be used to monitor shoe performance. In an alternative embodiment, the data can be transmitted (e.g., via radio waves) to a device with a display panel located with the user. For example, the data can be transmitted to a wristwatch or other device being worn the user. In response to the data, the user may adjust certain characteristics of the shoe by pressing buttons on the wristwatch, as described above. These adjustments are transmitted back the system 106 where the adjustments are implemented.

Figure 7:
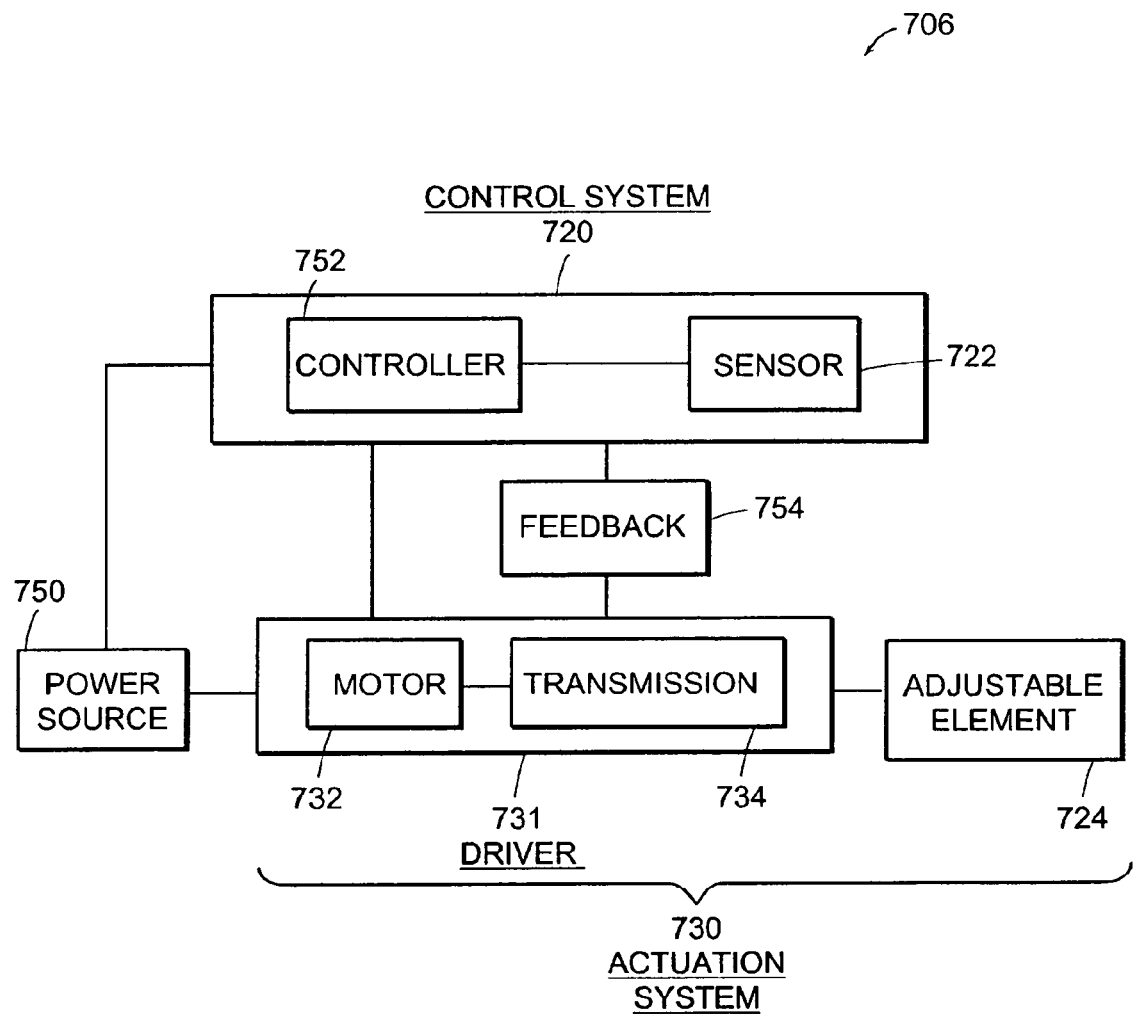
FIG. 7 is a block diagram of an intelligent system in accordance with the invention.

A block diagram of one embodiment of an intelligent system 106 is shown in FIG. 7. The intelligent system 706 includes a power source 750 electrically coupled to a control system 720 and an actuation system 730. The control system 720 includes a controller 752, for example one or more microprocessors, and a sensor 722. The sensor may be a proximity-type sensor and magnet arrangement. In one embodiment, the controller 152 is a microcontroller such as the PICMicro® manufactured by Microchip Technology Incorporated. In another embodiment, the controller 152 is a microcontroller manufactured by Cypress Semiconductor Corporation. The actuation system 730 includes a driver 731, including a motor 732 and a transmission element 734, and an adjustable element 724. The driver 731 and control system 720 are in electrical communication. The adjustable element 724 is coupled to the driver 731.

Optionally, the actuation system 730 could include a feedback system 754 coupled to or as part of the control system 720. The feedback system 754 may indicate the position of the adjustable element 724. For example, the feedback system 754 can count the number of turns of the motor 732 or the position of the limiter 728 (not shown). The feedback system 734 could be, for example, a linear potentiometer, an inductor, a linear transducer, or an infrared diode pair.

Figure 8:
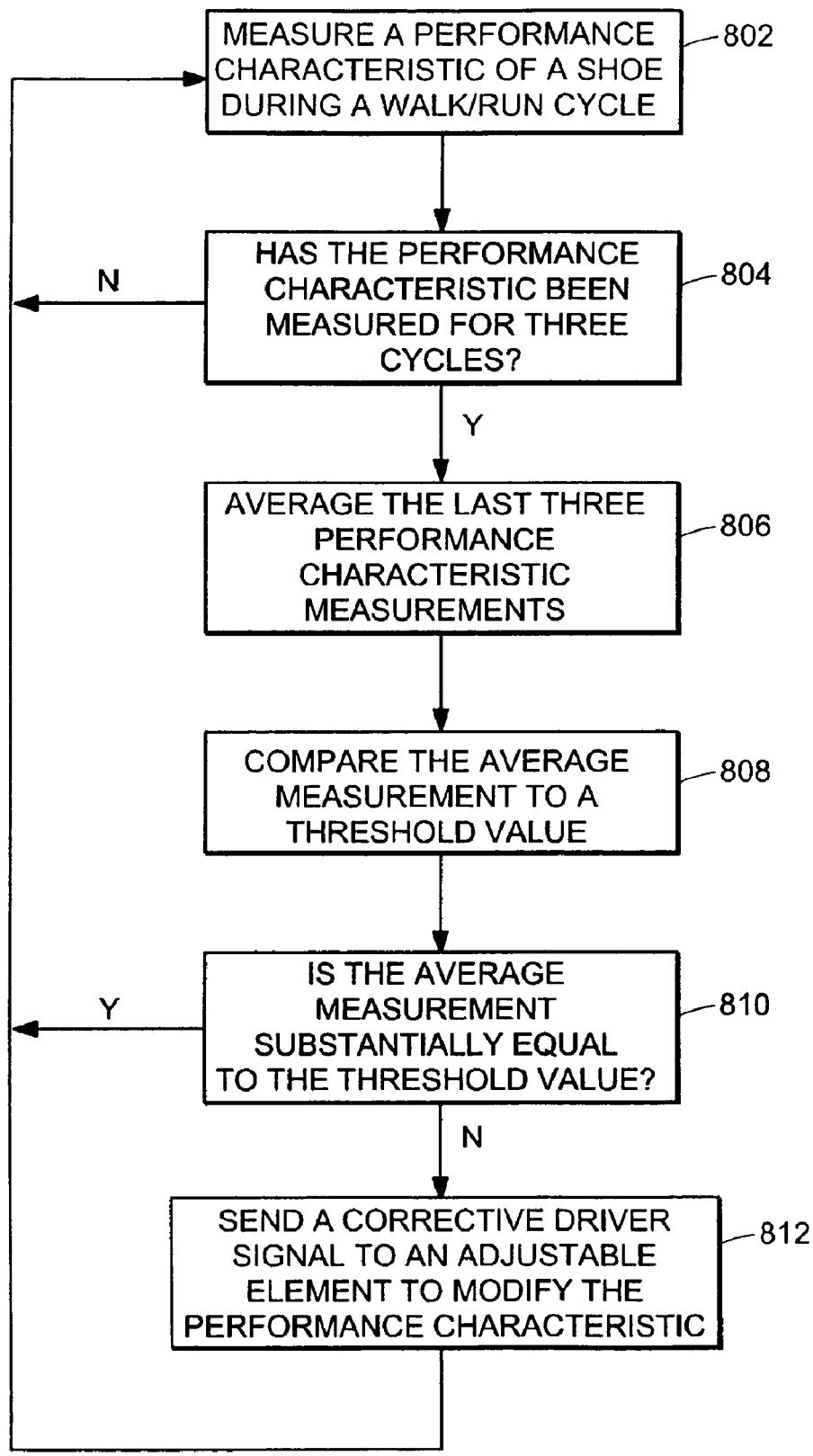
FIG. 8 is a flow chart depicting one mode of operation of the intelligent system of FIG. 1.

FIG. 8 depicts one possible algorithm for use with the intelligent system 106. The intelligent system 106 measures a performance characteristic of a shoe during a walk/run cycle. Before the system 106 begins to operate, the system 106 may run a calibration procedure after first being energized or after first contacting the ground surface. For example, the system 106 may actuate the adjustable element 124 to determine the position of the limiter 128 and/or to verify the range of the limiter 128, i.e., fully open or fully closed. During operation, the system 106 measures a performance characteristic of the shoe (step 802). In one embodiment, the measurement rate is about 300 Hz to about 60 KHz. The control system 120 determines if the performance characteristic has been measured at least three times (step 804) or some other predetermined number. If not, the system 106 repeats step 802 by taking additional measurements of the performance characteristic until step 804 is satisfied. After three measurements have been taken, the system 106 averages the last three performance characteristic measurements (step 806). The system 106 then compares the average performance characteristic measurement to a threshold value (step 808). At step 810, the system 106 determines if the average performance characteristic measurement is substantially equal to the threshold value. If the average performance characteristic measurement is substantially equal to the threshold value, the system 106 returns to step 802 to take another performance characteristic measurement. If the average performance characteristic measurement is not substantially equal to the threshold value, the system 106 sends a corrective driver signal to the adjustable element 124 to modify the performance characteristic of the shoe. The intelligent system 106 then repeats the entire operation until the threshold value is reached and for as long as the wearer continues to use the shoes. In one embodiment, the system 106 only makes incremental changes to the performance characteristic so that the wearer does not sense the gradual adjustment of the shoe and does not have to adapt to the changing performance characteristic. In other words, the system 106 adapts the shoe to the wearer, and does not require the wearer to adapt to the shoe.

Generally, in a particular application, the system 106 utilizes an optimal midsole compression threshold (target zone) that has been defined through testing for a preferred cushioning level. The system 106 measures the compression of the midsole 110 on every step, averaging the most recent three steps. If the average is larger than the threshold then the midsole 110 has over-compressed. In this situation, the system 106 signals the driver 131 to adjust the adjustable element 124 in a hardness direction. If the average is smaller than the threshold, then the midsole 110 has under-compressed. In this situation, the system 106 signals the driver 131 to adjust the adjustable element in a softness direction. This process continues until the measurements are within the target threshold of the system. This target threshold can be modified by the user to be harder or softer. This change in threshold is an offset from the preset settings. All of the above algorithm is computed by the control system 120.

In this particular application, the overall height of the midsole 110 and adjustable element 124 is about 20 mm. During testing, it has been determined that an optimal range of compression of the midsole 10 is about 9 mm to about 12 mm, regardless of the hardness of the midsole 10. In one embodiment, the limiter 128 has an adjustment range that corresponds to about 10 mm of vertical compression. The limiter 128, in one embodiment, has a resolution of less than or equal to about 0.5 mm. In an embodiment of the system 106 with user inputs, the wearer may vary the compression range to be, for example, about 8 mm to about 11 mm or about 10 mm to about 13 mm. Naturally, ranges of greater than 3 mm and lower or higher range limits are contemplated.

During running, the wearer's foot goes through a stride cycle that includes a flight phase (foot in the air) and a stance phase (foot in contact with the ground). In a typical stride cycle, the flight phase accounts for about ⅔ of the stride cycle. During the stance phase, the wearer's body is normally adapting to the ground contact. In a particular embodiment of the invention, all measurements are taken during the stance phase and all adjustments are made during the flight phase. Adjustments are made during the flight phase, because the shoe and, therefore, the adjustable element are in an unloaded state, thereby requiring significantly less power to adjust than when in a loaded state. In most embodiments, the shoe is configured such that the motor does not move the adjustable element, therefore lower motor loads are required to set the range of the adjustable element. In the embodiments depicted in FIGS. 15, 16, and 17, however, the adjustable element does move, as described in greater detail hereinbelow.

During operation the system 106 senses that the shoe has made contact with the ground. As the shoe engages the ground, the sole 104 compresses and the sensor 122 senses a change in the magnetic field of the magnet 123. The system 106 determines that the shoe is in contact with the ground when the system 106 senses a change in the magnetic field equal to about 2 mm in compression. It is also at this time that the system 106 turns off the power to the actuation system 130 to conserve power. During the stance phase, the system 106 senses a maximum change in the magnetic field and converts that measurement into a maximum amount of compression. In alternative embodiments, the system 106 may also measure the length of the stance phase to determine other performance characteristics of the shoe, for example velocity, acceleration, and jerk.

If the maximum amount of compression is greater than 12 mm, then the sole 104 has over-compressed, and if the maximum amount of compression is less than 9 mm, then the sole 104 has under-compressed. For example, if the maximum compression is 16 mm, then the sole 104 has over-compressed and the control system 120 sends a signal to the actuation system 130 to make the adjustable element 124 firmer. The actuation system 130 operates when the shoe is in the flight phase, i.e., less than 2 mm of compression. Once the system 106 senses that the compression is within the threshold range, the system 106 continues to monitor the performance characteristic of the shoe, but does not further operate the actuation system 130 and the adjustable element 124. In this way, power is conserved.

In alternative embodiments, the intelligent system 106 can use additional performance characteristics alone or in combination with the optimal midsole compression characteristic described above. For example, the system 106 can measure, in addition to compression, time to peak compression, time to recovery, and the time of the flight phase. These variables can be used to determine an optimum setting for the user, while accounting for external elements such as ground hardness incline, and speed. Time to peak compression is described as the amount of time that it takes from heel strike to the maximum compression of the sole while accounting for surface changes. It may be advantageous to use the area under a time versus compression curve to determine the optimum compression setting. This is in effect a measure of the energy absorbed by the shoe. In addition, the time of the flight phase (described above) can contribute to the determination of the optimum setting. The stride frequency of the user can be calculated from this variable. In turn, stride frequency can be used to determine changes in speed and to differentiate between uphill and downhill motion.

Figure 9A:
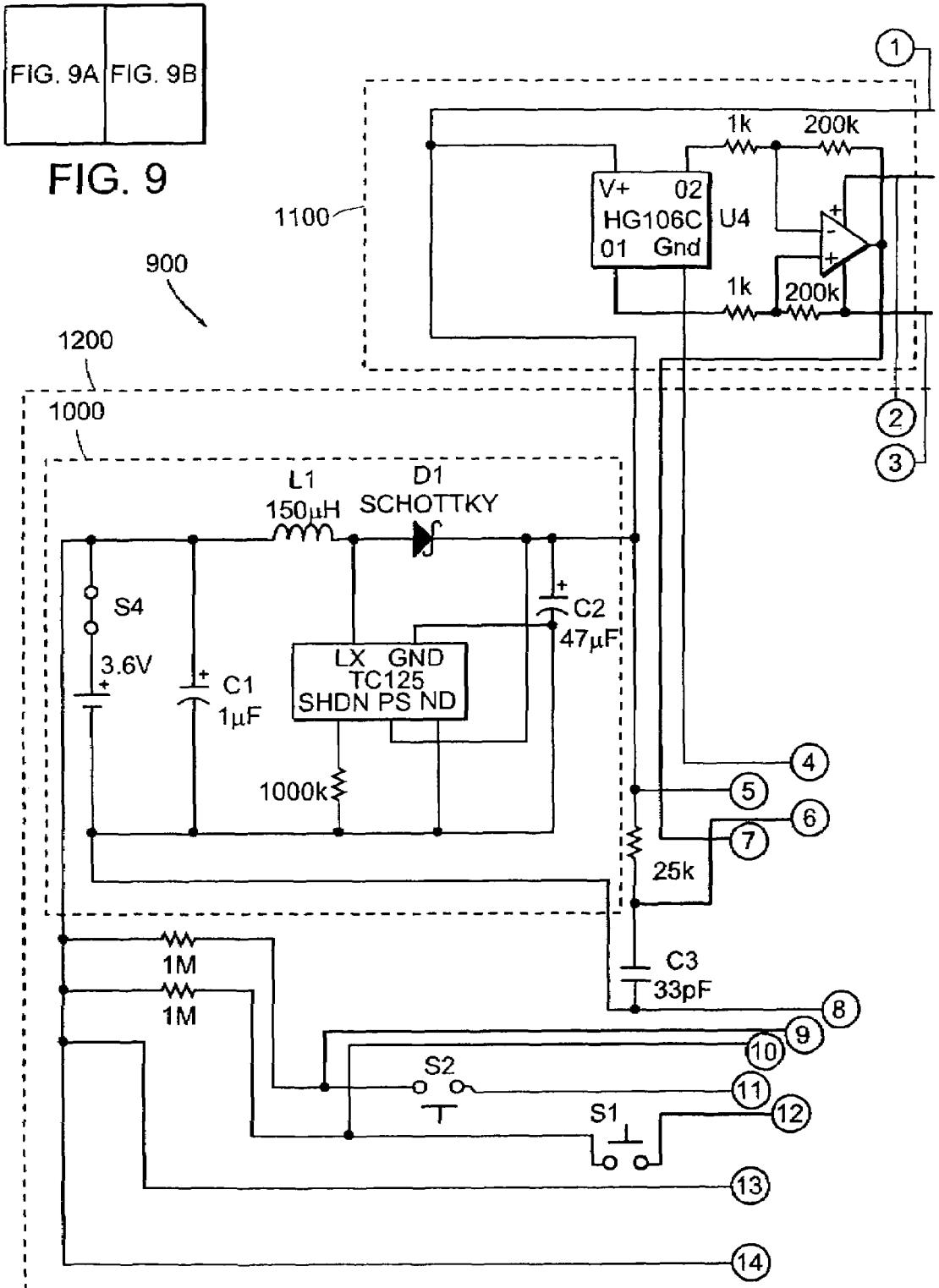
FIG. 9 is a circuit diagram of one embodiment of the intelligent system of FIG. 1.
Figure 9B:
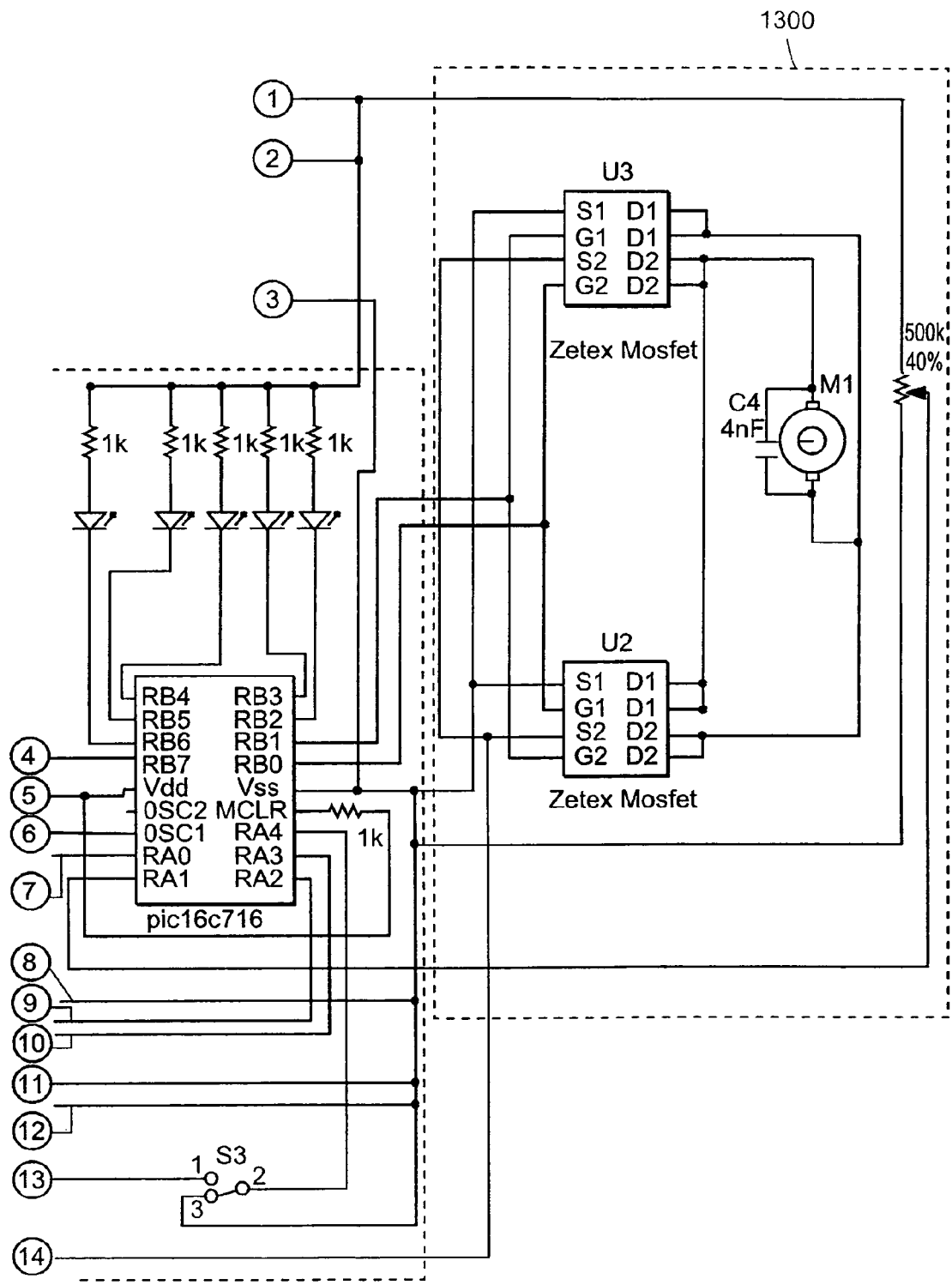
Figure 10:
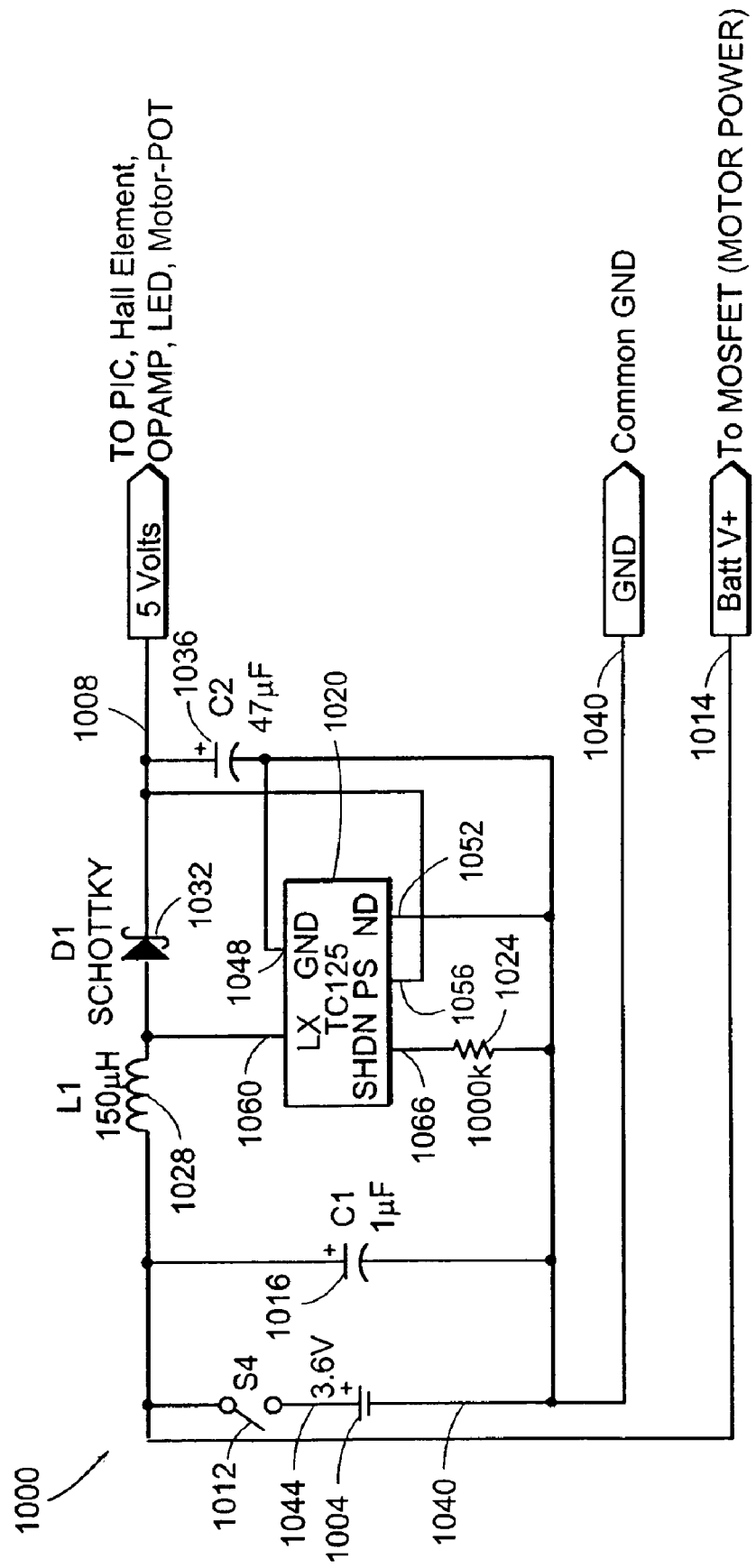
FIG. 10 is a circuit diagram of the voltage regulator system of FIG. 9.

FIG. 9 illustrates one embodiment of an electrical circuit 900 suitable for implementing an intelligent system 106 in accordance with the invention. The electrical circuit 900 includes a sensing system 1100 (FIG. 11), a control system 1200 (FIG. 12), and an actuation system 1300 (FIG. 13). The control system 1200 further includes a voltage regulator system 1000 (FIG. 10).

The voltage regulator system 1000 is a step-up DC/DC voltage regulator system; however, other types of voltage regulator systems are possible, including no voltage regulator system. Referring to FIG. 10, the input voltage of a power supply 1004 is stepped up to a higher voltage at the output 1008 of the voltage regulator system 1000. In the embodiment shown, the voltage regulator system 1000 includes the power supply 1004, a switch 1012, an input bypass capacitor 1016, and a TC125 PFM step-up DC/DC regulator 1020 coupled to an external resistor 1024, an inductor 1028, an output diode 1032, an output capacitor 1036, and three connection points (output 1008, ground 1040, and output 1014). The power supply 1004 is a 3.6 volt DC battery and the stepped-up voltage is 5 volts DC at the output 1008 of the voltage regulator system 1000. The switch 1012 acts as a basic on/off switch for the electrical circuit 900 (not shown). With the switch 1012 closed, the input bypass capacitor 1016 is connected in parallel with the power supply 1004. The ground 1040 of the power supply 1004 is connected to the ground terminal pin 1048 of the TC125 regulator 1020 and to a pin 1052 of the TC125 regulator 1020. The output 1008 of the voltage regulator system 1000 is connected to the power and voltage sense input pin 1056 of the TC125 regulator 1020. The output 1008 of the voltage regulator system 1000 provides both internal chip power and feedback voltage sensing for closed-loop regulation to the TC125 regulator 1020. The external inductor 1028 is connected, when switch 1012 is closed, between the positive terminal 1044 of the power supply 1004 and the inductor switch output pin 1060 of the TC125 regulator 1020. The output diode 1032, which, in the embodiment shown, is a Schottky diode, is connected between the inductor switch output pin 1060 and the power and voltage sense input pin 1056 of the TC125 regulator 1020. The output capacitor 1036 is connected between the ground 1040 of the power supply 1004 and the power and voltage sense input pin 1056 of the TC125 regulator 1020. The resistor 1024 is connected between the shutdown input pin 1066 of the TC125 regulator 1020 and the ground 1040 of the power supply 1004.

Figure 11:
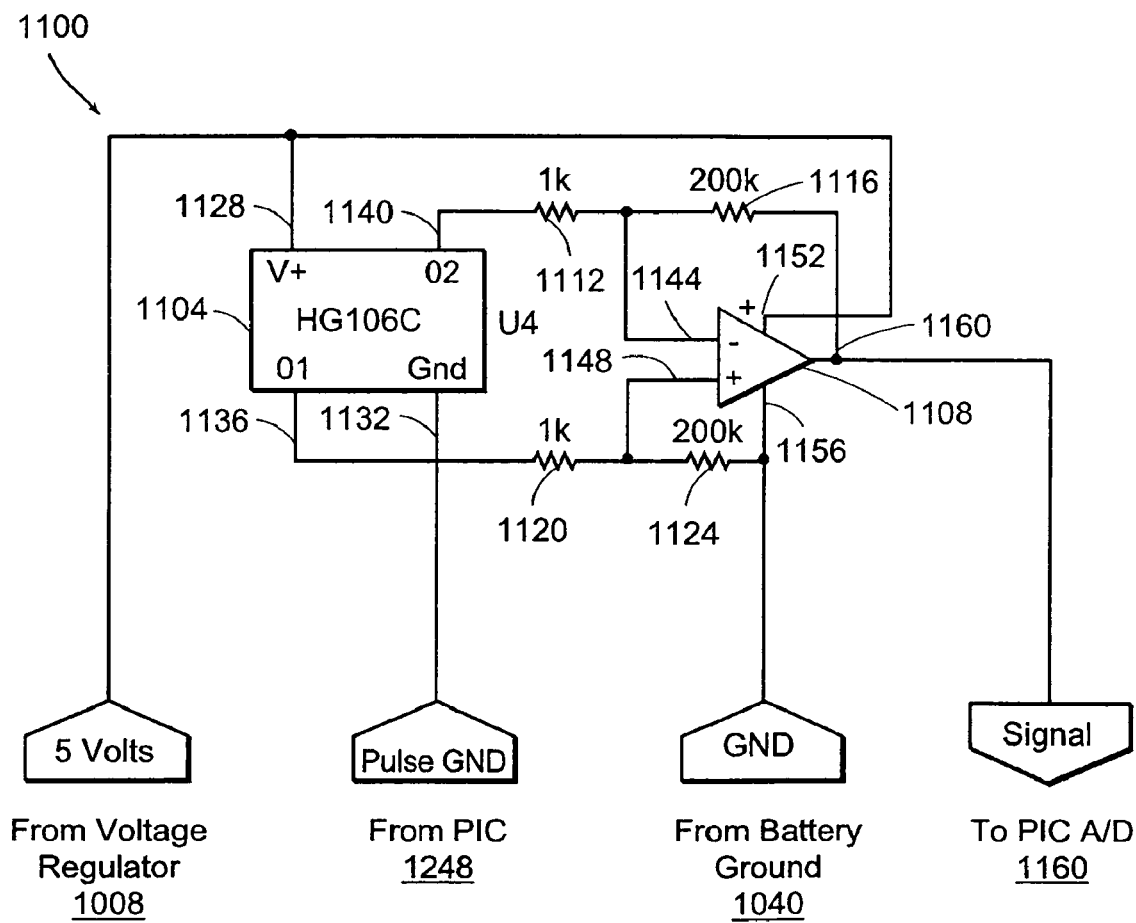
FIG. 11 is a circuit diagram of the sensing system of FIG. 9.

Referring to FIG. 11, the sensing system 1100 includes a hall element 1104, an operational amplifier ("op amp") 1108, and resistors 1112, 1116, 1120, and 1124. In an alternate embodiment, the hall element 1104 and the op amp 1108 may be replaced with a hall sensor that provides the equivalent functionality in a single package. The op amp 1108, as described below, produces a pulsed output signal. Alternatively, the output 1008 of the voltage regulator system 1000 is connected to a terminal 1128 of the sensor 1104 and provides power to the sensor 1104. A micro-controller 1204 of the control system 1200 is connected to a terminal 1132 of the sensor 1104 via connection point 1248. See FIG. 12. The micro-controller 1204 alternately pulses the sensor 1104 on, by sending it a ground signal, and then off. The sensor 1104 is pulsed on to measure magnetic field strength, as described above, and then off to conserve power. When pulsed on, the sensor 1104 outputs voltages at its terminals 1136 and 1140. The resistor 1112 is connected between the terminal 1140 of the sensor 1104 and the inverting input 1144 of the op amp 1108. The resistor 1120 is connected between the terminal 1136 of the sensor 1104 and the non-inverting input 1148 of the op amp 1108. The resistor 1116 is connected between the inverting input 1144 of the op amp 1108 and the micro-controller 1204 of the control system 1200 via connection point 1160. The resistor 1124 is connected between the non-inverting input 1148 of the op-amp 1108 and the ground 1040 of the power supply 1004 of the voltage regulator system 1000. The positive supply voltage terminal 1152 of the op amp 1108 is connected to the output 1008 of the voltage regulator system 1000 and the negative supply voltage terminal 1156 of the op amp 1108 is connected to the ground 1040 of the power supply 1004 of the voltage regulator system 1000. In the embodiment shown, the op amp 1108 amplifies the difference in voltage between the terminal 1136 and the terminal 1140 of the hall effect sensor 1104. With a 1 kΩ resistor 1112, a 200 kΩ resistor 1116, a 1 kΩ resistor 1120, and a 200 kΩ resistor 1124, the voltage at the op amp output 1160 is the difference in voltage between the terminal 1136 and the terminal 1140 of the sensor 1104 amplified by a factor of 200 (i.e., V1160=200 [V1136-V1140]). Other amplification factors may be achieved by choosing appropriate resistances for resistors 1112, 1116, 1120, and 1124. The op amp output 1160 is connected to micro-controller 1204 of the control system 1200. The pulsed output signal of the op amp 1108 is thus inputted to the micro-controller 1204.

Figure 12A:
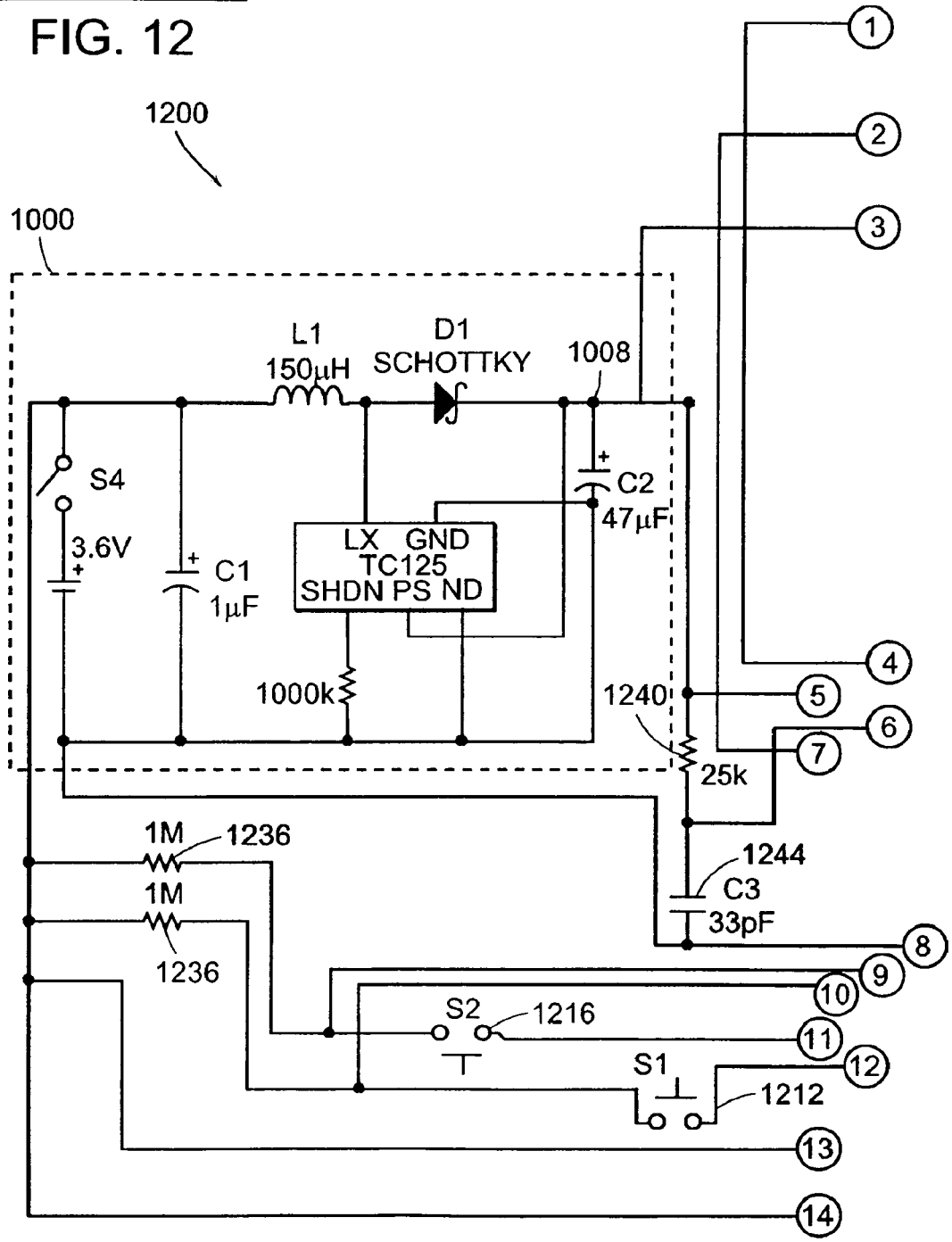
FIG. 12 is a circuit diagram of the control system of FIG. 9.
Figure 12B:
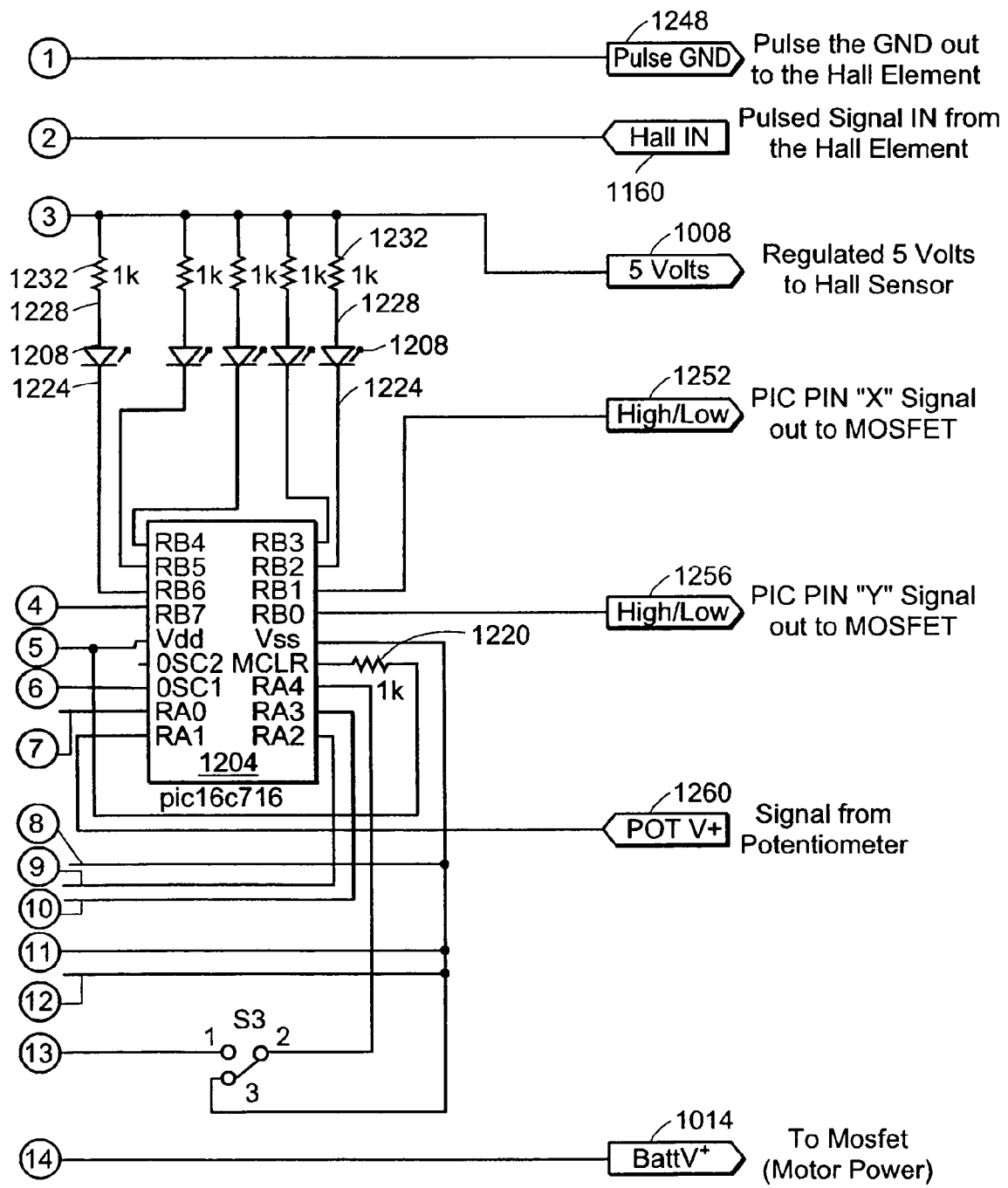
Figure 13:
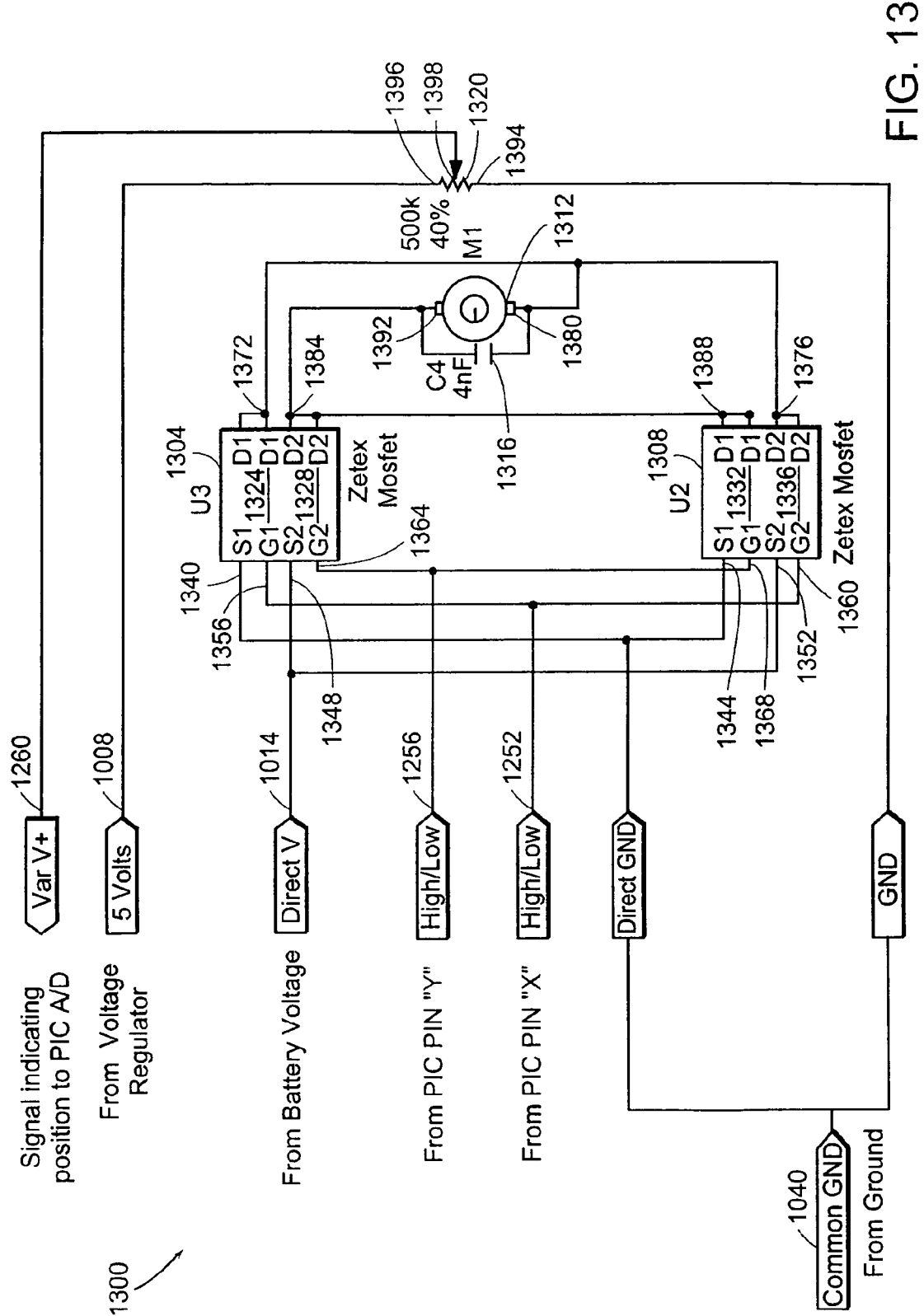
FIG. 13 is a circuit diagram of the actuation system of FIG. 9.

Referring to FIG. 12, the control system 1200 includes the voltage regulator system 1000, a micro-controller 1204, light emitting diodes ("LEDs") 1208, two switches 1212, 1216, and an external RC oscillator including a resistor 1240 and a capacitor 1244. The output 1008 of the voltage regulator system 1000 is connected to the micro-controller 1204 in order to power the micro-controller 1204. The output 1008 of the voltage regulator system 1000 is further connected through a resistor 1220 to a different pin of the micro-controller 1204 to allow for active low reset of the micro-controller 1204. The ground 1040 of the power supply 1004 is connected to the micro-controller 1204 to provide it with a ground reference. The LEDs 1208 provide a visual output to the user of, for example, the current softness/hardness setting of the midsole. The cathodes 1224 of the LEDs 1208 are connected to the micro-controller 1204 and the anodes 1228 of the LEDs 1208 are connected through resistors 1232 to the output 1008 of the voltage regulator system 1000. The micro-controller 1204 turns on or off one or several of the LEDs 1208. Switches 1212 and 1216 are connected between the ground 1040 of the power supply 1004 and, through resistors 1236, the positive terminal 1044 of the power supply 1004 when the switch 1012 is closed. Switches 1212 and 1216, when closed, connect various pins of the micro-controller 1204 to the ground 1040 of the power supply 1004. The user may adjust, for example, the midsole compression threshold by closing either switch 1212 or 1216 of the control system 1200. The user does so by actuating push buttons, located on the outside of the shoe, which control switches 1212 and 1216 of the control system 1200. The resistor 1240 of the external RC oscillator is connected between the output 1008 of the voltage regulator system 1000 and an input pin to the timing circuitry of the micro-controller 1204. The capacitor 1244 of the external RC oscillator is connected between the ground 1040 of the power supply 1004 and the same input pin to the timing circuitry of the micro-controller 1204.

Referring to FIG. 13, the actuation system 1300 includes transistor bridges 1304 and 1308, a motor 1312 connected in parallel with a capacitor 1316, and a potentiometer 1320. In the embodiment shown, the transistor bridge 1304 includes an n-Channel MOSFET 1324 and a p-Channel MOSFET 1328 and the transistor bridge 1308 includes an n-Channel MOSFET 1332 and a p-Channel MOSFET 1336. The source 1340 of MOSFET 1324 and the source 1344 of MOSFET 1332 are connected to the ground 1040 of the power supply 1004. The source 1348 of MOSFET 1328 and the source 1352 of MOSFET 1336 are connected to the output 1014 of the power supply 1004 when the switch 1012 is closed. The gate 1356 of MOSFET 1324 and the gate 1360 of MOSFET 1336 are connected to the X pin of the micro-controller 1204 via connection point 1252. The gate 1364 of MOSFET 1328 and the gate 1368 of MOSFET 1332 are connected to the Y pin of micro-controller 1204 via connection point 1256. The drain 1372 of MOSFET 1324 and the drain 1376 of MOSFET 1336 are connected to a terminal 1380 of the motor 1312. The drain 1384 of MOSFET 1328 and the drain 1388 of MOSFET 1332 are connected to a terminal 1392 of the motor 1312. In order to drive the motor 1312 in one direction, the micro-controller 1204 turns on MOSFETs 1324 and 1328 while MOSFETs 1332 and 1336 are turned off. In order to drive the motor 1312 in the opposite direction, the micro-controller 1204 turns on MOSFETs 1332 and 1336 while MOSFETs 1324 and 1328 are turned off. A terminal 1396 of the potentiometer 1320 is connected to the output 1008 of the voltage regulator system 1000 and a terminal 1394 of the potentiometer 1320 is connected to the ground 1040 of the power supply 1004. The voltage at the wiper terminal 1398 of the potentiometer 1320 is measured by the micro-controller 1204 via connection point 1260. Depending on the direction that the motor 1312 is made to turn by the micro-controller 1204, the wiper terminal 1398 of the potentiometer 1320 is moved in one direction or the other. The voltage at the wiper terminal 1398 of the potentiometer 1320 therefore indicates the position of the limiter 128 based on the number of turns that the motor 1312 has made.

Figure 14B:
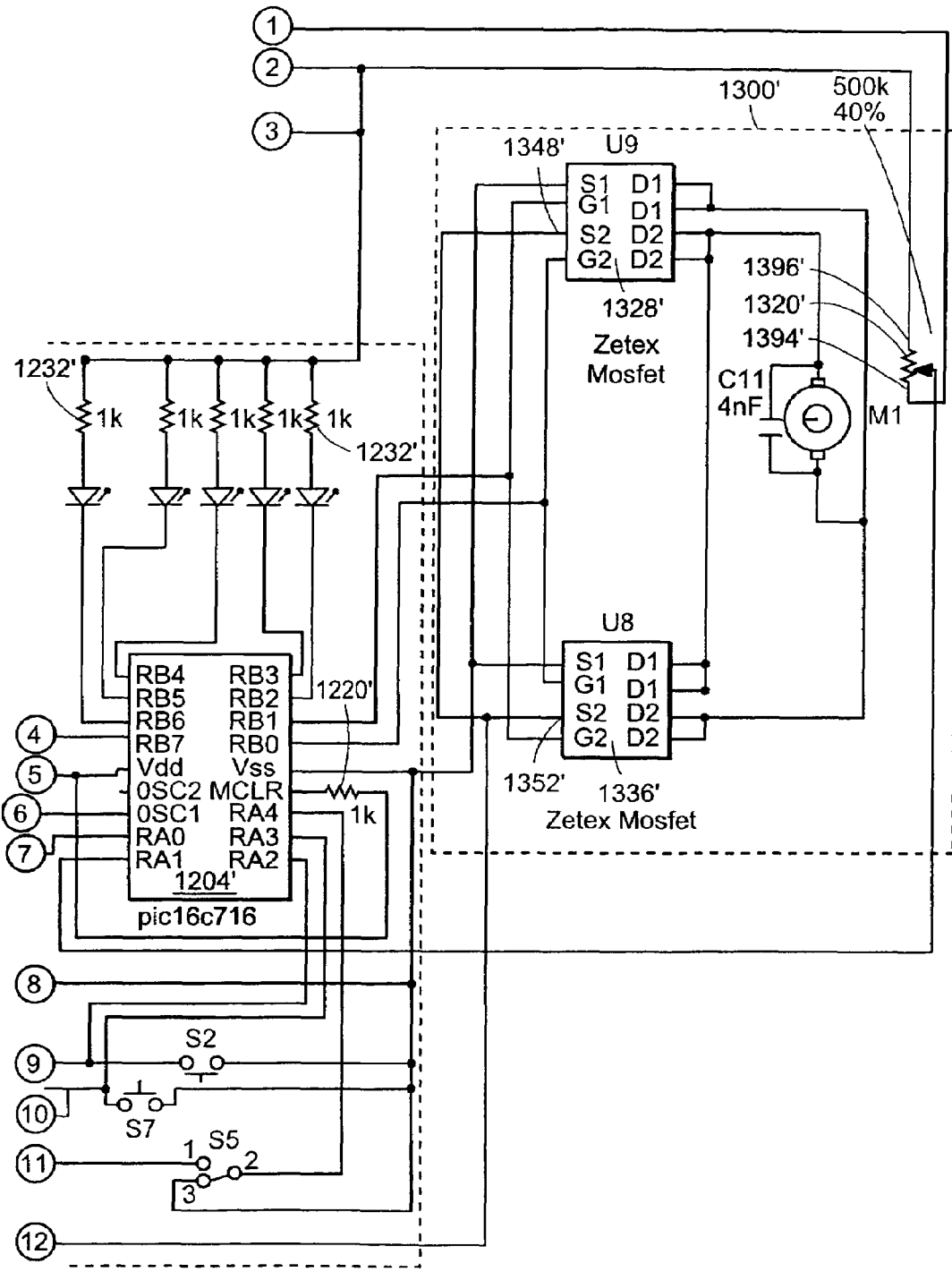
FIG. 14 is a circuit diagram of another embodiment of the intelligent system of FIG. 1.

FIG. 14 illustrates an alternative embodiment of an electrical circuit 900' suitable for implementing an intelligent cushioning system in accordance with the invention. As in the first embodiment, the electrical circuit 900' includes a sensing system 1100', a control system 1200', and an actuation system 1300'. Again, as in the first embodiment, the control system 1200' includes a voltage regulator system 1000'.

As opposed to the first embodiment, the voltage regulator system 1000' is a step-down DC/DC voltage regulator system. The input voltage of a power supply 1004' is stepped down to a lower voltage at the output 1008' of the voltage regulator system 1000'. In the embodiment shown, the voltage regulator system 1000' includes the power supply 1004', a switch 1012', an input capacitor 1404, an LTC3405A step-down DC/DC regulator 1408, an inductor 1412, an output capacitor 1416, resistors 1420 and 1424, and a capacitor 1428. The power supply 1004' is a 3.6 volt DC battery and the stepped-down voltage at the output 1008' of the voltage regulator system 1000' may be chosen by selecting appropriate resistances for the resistors 1420 and 1424. The switch 1012' acts as a basic on/off switch for the electrical circuit 900'. When the switch 1012' is closed, the input capacitor 1404 is connected in parallel with the power supply 1004'. Moreover, when the switch 1012' is closed, the positive terminal 1044' of the power supply 1004' is connected to the run control input pin 1432 and the main supply pin 1436 of the LTC3405A regulator 1408. The ground 1040' of the power supply 1004' is connected to the ground pin 1440 and the mode select input pin 1444 of the LTC3405A regulator 1408. The inductor 1412 is connected between the switch node connection to inductor pin 1448 of the LTC3405A regulator 1408 and the output 1008' of the voltage regulator system 1000'. The output capacitor 1416 is connected between the output 1008' of the voltage regulator system 1000' and the ground 1040' of the power supply 1004'. The resistor 1420 is connected between the feedback pin 1452 of the LTC3405A regulator 1408 and the ground 1040' of the power supply 1004'. The capacitor 1428 is connected in parallel with the resistor 1424. Both the resistor 1424 and the capacitor 1428 are connected between the feedback pin 1452 of the LTC3405A regulator 1408 and the output 1008' of the voltage regulator system 1000'.

The sensing system 1100', including a hall element type sensor 1104' and an op amp 1108', is similar to the sensing system 1100 of the electrical circuit 900. In an alternate embodiment, the hall element 1104' and the op amp 1108' may be replaced with a hall sensor that provides the equivalent functionality in a single package. The op amp 1108' produces the same output signal at its output 1160' as does the op amp 1108 at its output 1160; however, the sensing system 1100' is different in several respects. First, rather than being connected to the output of a step-up DC/DC voltage regulator system, the terminal 1128' of the sensor 1104' and the positive supply voltage terminal 1152' of the op amp 1108' are instead connected, when the switch 1012' is closed, to the positive terminal 1044' of the power supply 1004'. Second, the micro-controller 1204', in addition to being connected to a terminal 1132' of the sensor 1104', is also connected to the negative supply voltage terminal 1156' of the op amp 1108'. The micro-controller 1204', therefore, alternately pulses the op amp 1108' on and then off, to conserve power, in tandem with the sensor 1104'. Finally, the resistor 1124', rather than being connected to the ground 1040' of the power supply 1004', is instead connected to the pin of the micro-controller 1204' that is used to alternately pulse the sensor 1104' and the op amp 1108' on and then off. Nevertheless, when the micro-controller 1204' pulses a ground signal to the terminal 1132' and the negative supply voltage terminal 1156' to turn on the sensor 1104' and the op amp 1108', respectively, the resistor 1124' is effectively connected to the pulsed ground signal.

The control system 1200' is similar to the control system 1200 of the electrical circuit 900; however, the control system 1200' is different in several respects. First, rather than being connected to and powered by the output of a step-up DC/DC voltage regulator system, the micro-controller 1204' is, when the switch 1012' is closed, directly connected to the positive terminal 1044' of the power supply 1004' and therefore directly powered by the power supply 1004'. Second, rather than being connected to the output of a step-up DC/DC voltage regulator system, the resistors 1220', 1232', and 1240' are connected, when the switch 1012' is closed, to the positive terminal 1044' of the power supply 1004'.

The actuation system 1300' is similar to the actuation system 1300 of the electrical circuit 900; however, the actuation system 1300' is different in several respects. First, rather than being connected to the positive terminal 1044' of the power supply 1004' when the switch 1012' is closed, the source 1348' of MOSFET 1328' and the source 1352' of MOSFET 1336' are instead connected to the output 1008' of the voltage regulator system 1000'. Second, rather than being connected to the output of a step-up DC/DC voltage regulator system, the terminal 1396' of the potentiometer 1320' is instead connected, when the switch 1012' is closed, to the positive terminal 1044' of the power supply 1004'. Finally, rather than being connected to the ground 1040' of the power supply 1004', the terminal 1394' of the potentiometer 1320' is instead connected to the pin of the micro-controller 1204' that is used to alternately pulse the sensor 1104' and the op amp 1108' on and then off. Nevertheless, when the micro-controller 1204' pulses a ground signal to the terminal 1132' and the negative supply voltage terminal 1156' to turn on the sensor 1104' and the op amp 1108', respectively, the terminal 1394' of the potentiometer 1320' is effectively connected to the pulsed ground signal.

Figure 15A:
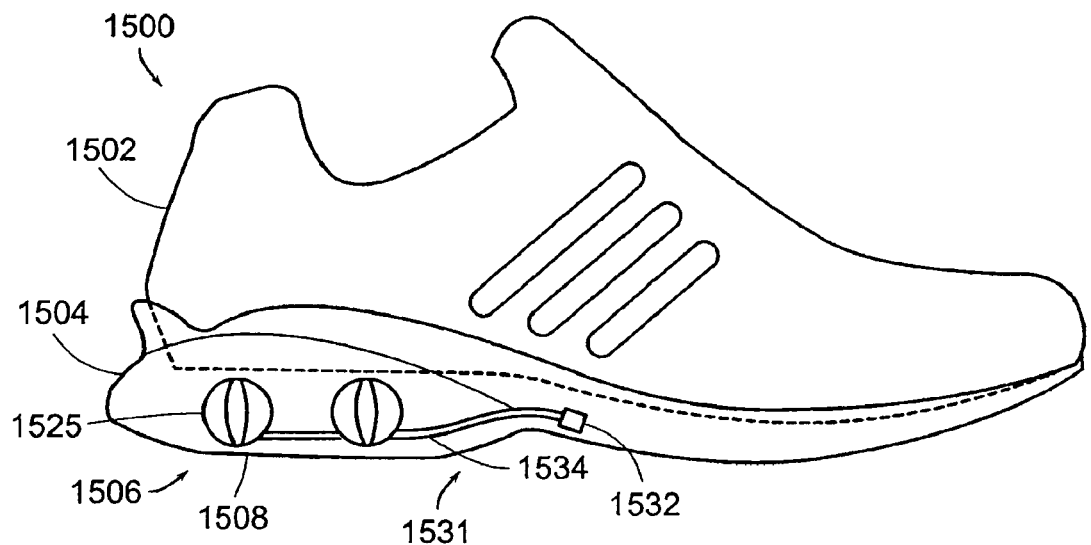
FIG. 15A is a schematic side view of an article of footwear including an alternative embodiment of an intelligent system in accordance with the invention.
Figure 15B:
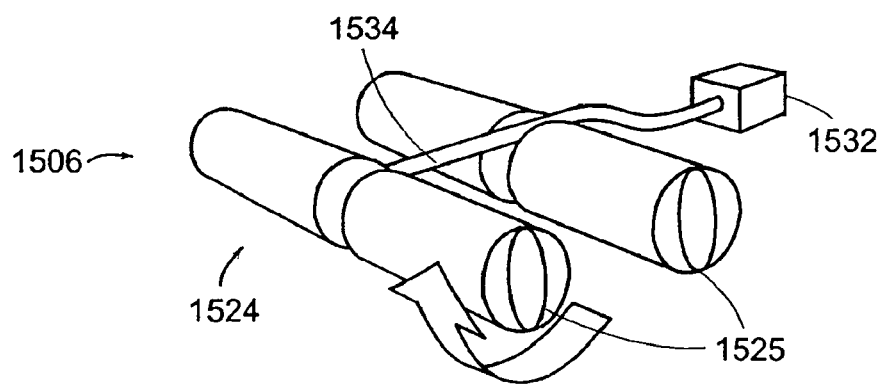
FIG. 15B is a schematic perspective view of a portion of the intelligent system of FIG. 15A.

FIGS. 15A and 15B depict an article of footwear 1500 including an alternative intelligent system 1506. The article of footwear 1500 includes an upper 1502, a sole 1504, and the intelligent system 1506. The intelligent system 1506 is disposed in the rearfoot portion 1508 of the sole 1504. The intelligent system 1506 includes a driver 1531 and an adjustable element 1524 of one or more similar components. The adjustable element 1524 is shown in greater detail in FIG. 15B and includes two dual density tuning rods 1525 that are rotated in response to a corrective driver signal to modify a performance characteristic of the footwear 1500. The dual density rods 1525 have an anisotropic property and are described in detail in pending U.S. patent application Ser. No. 10/144,440, the entire disclosure of which is hereby incorporated herein by reference. The dual density rods 1525 are rotated by the motor 1532 and the transmission element 1534 to make the sole 1504 harder or softer. The transmission element 1534 is coupled to the dual density rods 1525 at about a lateral midpoint of the rods 1525, for example by a rack and pinion or worm and wheel arrangement.

FIG. 16A depicts an article of footwear 1600 including an alternative intelligent system 1606. FIGS. 16B-16D depict the adjustable element 1624 in various states of operation. The article of footwear 1600 includes an upper 1602, a sole 1604, and the intelligent system 1606. The intelligent system 1606 includes a driver 1631 and an adjustable element 1624. The adjustable element 1624 includes two multi-density plates 1625, 1627. One of the plates, in this embodiment lower plate 1627, is slid relative to the other plate, in this embodiment upper plate 1625, by the driver 1631, in response to the corrective driver signal to modify the performance characteristic of the shoe (arrow 1680).

The plates 1625, 1627 are made of alternating density materials. In particular, the plates 1625, 1627 are made up of alternating strips of a relatively soft material 1671 and a relatively hard material 1673. The alignment of the different density portions of the plates 1625, 1627 determines the performance characteristic of the shoe. In FIG. 16B, the relatively hard materials 1673 are substantially aligned, thereby resulting in a relatively hard adjustable element 1624. In FIG. 16C, the different density materials 1671, 1673 are only partially aligned, thereby resulting in a softer adjustable element 1624. In FIG. 16D, the relatively hard materials 1673 and the relative soft materials 1671 are substantially aligned, thereby resulting in the softest possible adjustable element 1624.

Figure 17A:
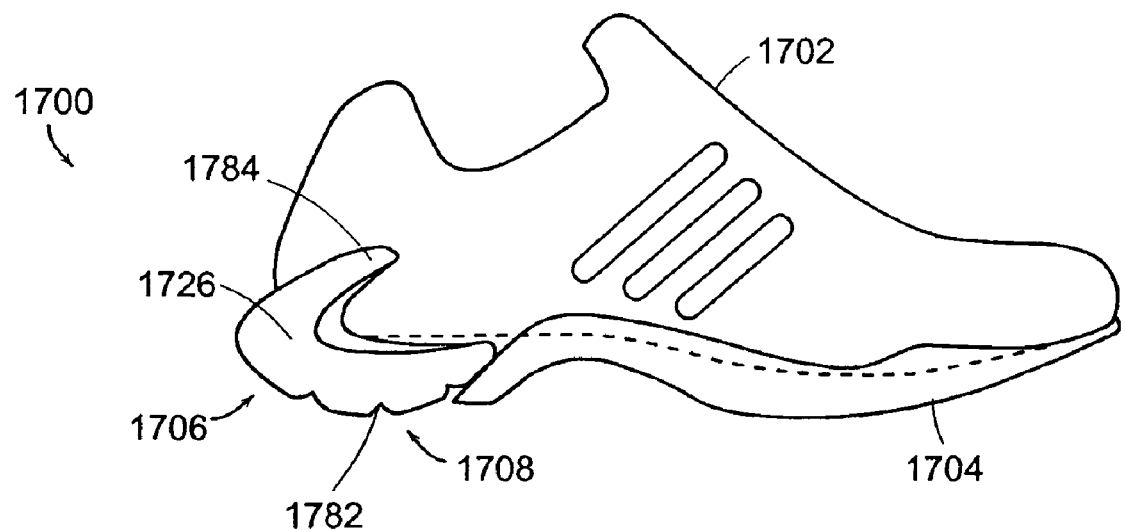
FIG. 17A is a schematic side view of an article of footwear including yet another alternative embodiment of an intelligent system in accordance with the invention.
Figure 17B:
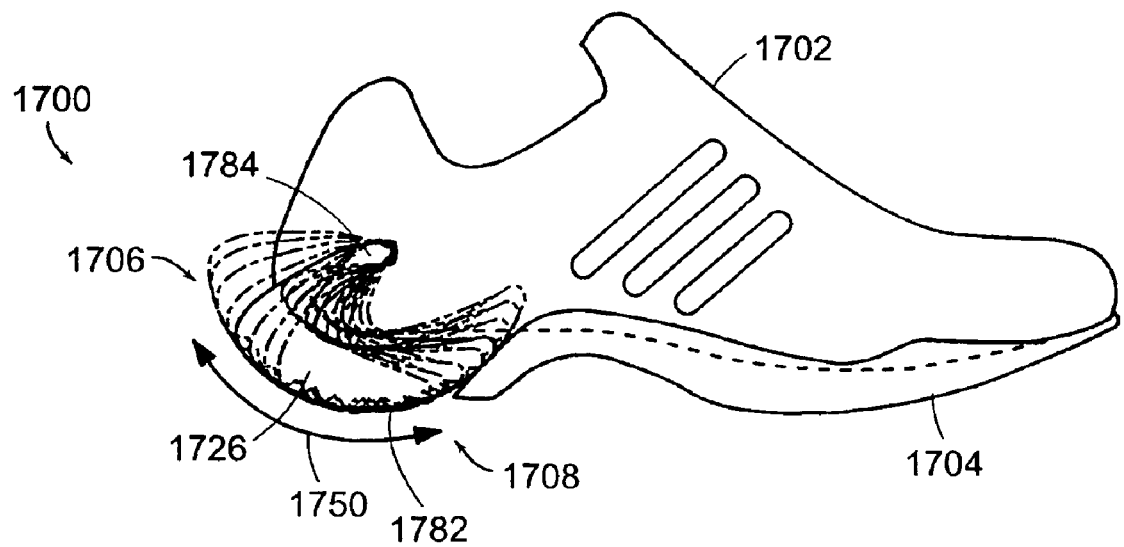
FIG. 17B is a schematic side view of the intelligent system of FIG. 17A throughout a range of adjustment.

FIGS. 17A and 17B depict an article of footwear 1700 including an alternative intelligent system 1706. The article of footwear 1700 includes an upper 1702, a sole 1704, and the intelligent system 1706. The intelligent system 1706 is disposed in the rearfoot portion 1708 of the sole 1704. The intelligent system 1706 includes a driver 1731 (not shown, but similar to those described hereinabove) and an adjustable element 1724. The adjustable element 1724 is a multi-density heel portion 1726 that swivels relative to the sole 1704 (see arrow 1750 in FIG. 17B). Swiveling the heel portion 1726 modifies the mechanical properties of the footwear 1700 at a heel strike zone 1782. The heel portion 1726 swivels about a pivot point 1784 in response to a force from the driver 1731.

The various components of the adjustable elements described herein can be manufactured by, for example, injection molding or extrusion and optionally a combination of subsequent machining operations. Extrusion processes may be used to provide a uniform shape, such as a single monolithic frame. Insert molding can then be used to provide the desired geometry of the open spaces, or the open spaces could be created in the desired locations by a subsequent machining operation. Other manufacturing techniques include melting or bonding additional elements. For example, the cylinders 448 may be joined with a liquid epoxy or a hot melt adhesive, such as ethylene vinyl acetate (EVA). In addition to adhesive bonding, components can be solvent bonded, which entails using a solvent to facilitate fusing of various components or fused together during a foaming process.

The various components can be manufactured from any suitable polymeric material or combination of polymeric materials, either with or without reinforcement. Suitable materials include: polyurethanes, such as a thermoplastic polyurethane (TPU); EVA; thermoplastic polyether block amides, such as the Pebax® brand sold by Elf Atochem; thermoplastic polyester elastomers, such as the Hytrel® brand sold by DuPont; thermoplastic elastomers, such as the Santoprene® brand sold by Advanced Elastomer Systems, L.P.; thermoplastic olefin; nylons, such as nylon 12, which may include 10 to 30 percent or more glass fiber reinforcement; silicones; polyethylenes; acetal; and equivalent materials. Reinforcement, if used, may be by inclusion of glass or carbon graphite fibers or para-aramid fibers, such as the Kevlar® brand sold by DuPont, or other similar method. Also, the polymeric materials may be used in combination with other materials, for example natural or synthetic rubber. Other suitable materials will be apparent to those skilled in the art.

In a particular embodiment, the expansion element 126 can be made of one or more various density foams, non-foamed polymer materials, and/or skeletal elements. For example, the cylinder could be made of Hytrel® 4069 or 5050 with a 45 Asker C foamed EVA core. In another embodiment, the cylinder is made of Hytrel® 5556 without an inner core foam. The expansion element 126 can have a hardness in the range of about 40 to about 70 Asker C, preferably between about 45 and about 65 Asker C, and more preferably about 55 Asker C. In an alternative embodiment, the tuning rods 1525, the multiple density plates 1625, 1627, or the upper and lower support plates 114, 116 may be coated with an anti-friction coating, such as a paint including Teflon® material sold by DuPont or a similar substance. The various components can be color coded to indicate to a wearer the specific performance characteristics of the system and clear windows can be provided along the edge of the sole. The size and shape of the various components can vary to suit a particular application. In one embodiment, the expansion element 126 can be about 10 mm to about 40 mm in diameter, preferably about 20 mm to about 30 mm, and more preferably about 25 mm. The length of the expansion element 126 can be about 50 mm to about 100 mm, preferably about 75 mm to about 90 mm, and more preferably 85 mm.

In addition, the expansion element 126 can be integrally formed by a process called reverse injection, in which the cylinder 142 itself forms the mold for the foam core 144. Such a process can be more economical than conventional manufacturing methods, because a separate core mold is not required. The expansion element 126 can also be formed in a single step called dual injection, where two or more materials of differing densities are injected simultaneously to create integrally the cylinder 142 and the core 144.

Figure 18:
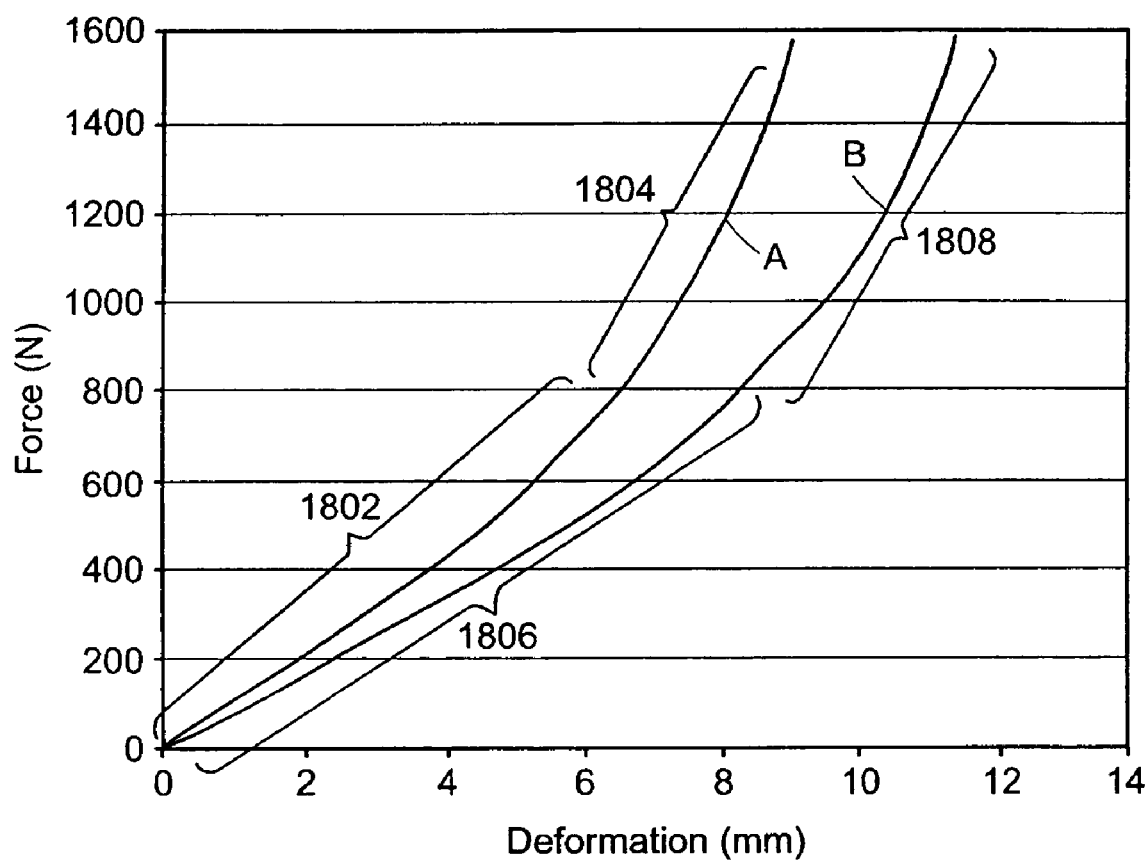
FIG. 18 is a graph depicting a performance characteristic of a specific embodiment of an adjustable element.

FIG. 18 is a graph depicting a performance characteristic of an adjustable element at two different settings (curves A and B). The graph depicts the amount of deformation of the adjustable element in a loaded condition, i.e., under compression. As can be seen, each curve A, B has two distinct slopes 1802, 1804, 1806, 1808. The first slope 1802, 1806 of each curve generally represents the adjustable element from first contact until the adjustable element contacts the limiter. During this phase, the resistance to compression comes from the combined effect of the structural wall and core of the adjustable element, which compress when loaded. The second slope 1804, 1808 of each curve represents the adjustable element under compression while in contact with the limiter. During this phase, very little additional deformation of the adjustable element is possible and the additional force attempts to bend or buckle the structural wall.

At setting A, which is a relatively hard setting, the adjustable element deforms about 6.5 mm when a force of 800 N is applied to the adjustable element, as represented by slope 1802. At this point, the adjustable element has contacted the limiter and very little additional deformation is possible. As slope 1804 represents, the additional deformation of the adjustable element is only about 2 mm after an additional force of 800 N is applied to the adjustable element. At setting B, which is a relatively soft setting, the adjustable element deforms about 8.5 mm when a force of 800 N is applied to the adjustable element, as represented by slope 1806. At this point, the adjustable element has contacted the limiter and very little additional deformation is possible. As slope 1808 represents, the additional deformation of the adjustable element is only about 2.5 mm after an additional force of 800 N is applied to the adjustable element.

Figure 19:
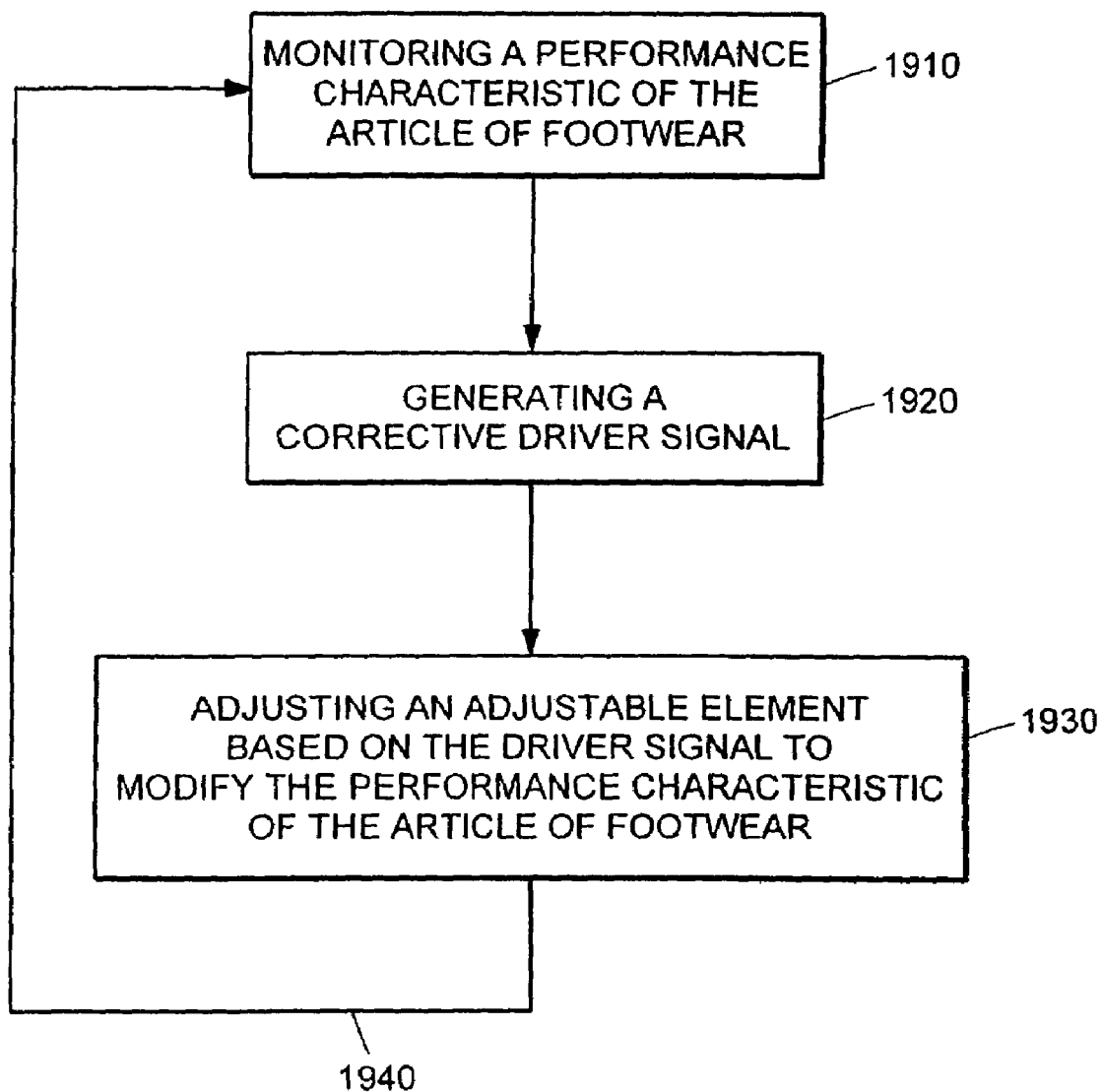
FIG. 19 is a flow chart depicting one embodiment of a method of modifying a performance characteristic of an article of footwear during use.

FIG. 19 depicts a flow chart representing a method of modifying a performance characteristic of an article of footwear during use. The method includes monitoring the performance characteristic of the article of footwear (step 1910), generating a corrective driver signal based on the monitored performance characteristic (step 1920), and adjusting an adjustable element based on the driver signal to modify the performance characteristic of the article of footwear (step 1930). In a particular embodiment, the steps are repeated until a threshold value of the performance characteristic is obtained (step 1940).

Figure 20A:
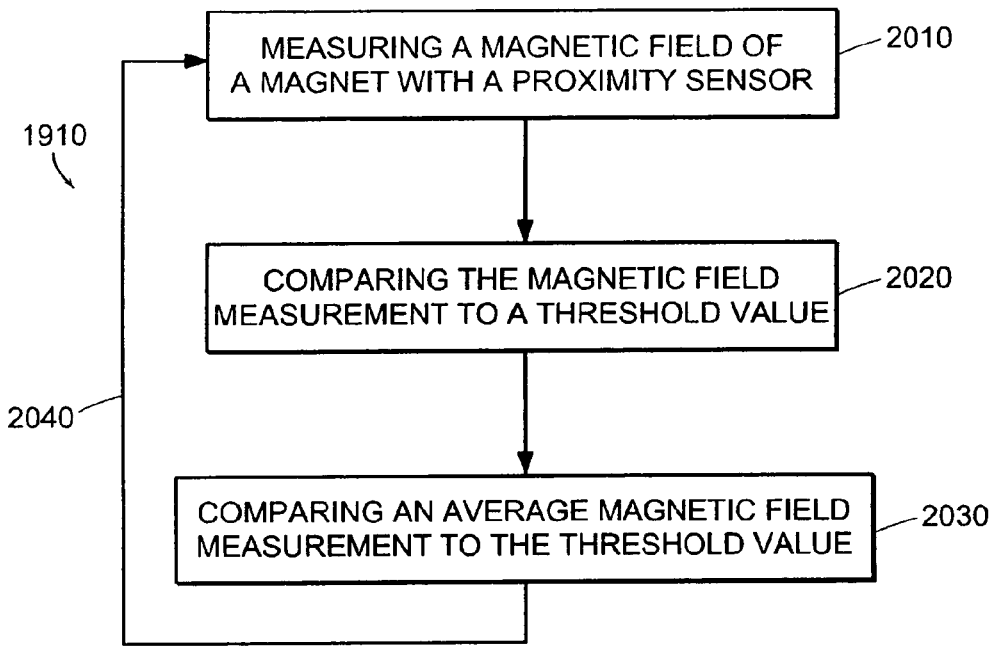
FIGS. 20A and 20B are flow charts depicting additional embodiments of the method of FIG. 19.

One possible embodiment of the monitoring step 1910 is expanded in FIG. 20A. As shown, monitoring the performance characteristic involves measuring a magnetic field of a magnet with a proximity-type sensor (substep 2010) and comparing the magnetic field measurement to a threshold value (substep 2020). Optionally, monitoring the performance characteristic may include taking multiple measurements of the magnetic field and taking an average of some number of measurements. The system then compares the average magnetic field measurement to the threshold value (optional substep 2030). The system could repeat these steps as necessary (optional substep 2040) until the magnetic field measurement is substantially equal to the threshold value, or within a predetermined value range.

Figure 20B:
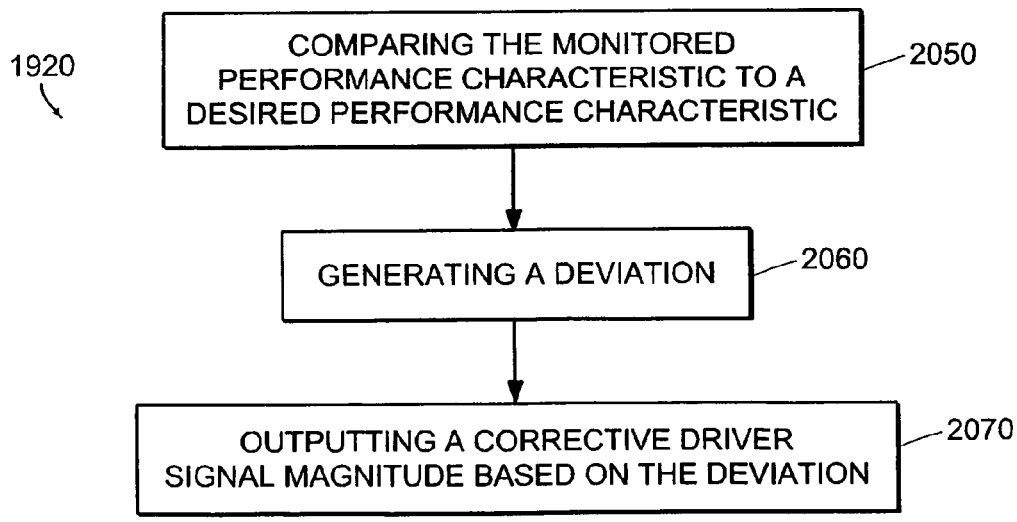

One possible embodiment of the generating step 1920 is expanded in FIG. 20B. As shown, generating the corrective driver signal involves comparing the monitored performance characteristic to a desired performance characteristic (substep 2050), generating a deviation (substep 2060), and outputting a corrective driver signal magnitude based on the deviation (substep 2070). In one embodiment, the corrective driver signal has a predetermined magnitude, such that a predetermined amount of correction is made to the performance characteristic. In this way, the system makes incremental changes to the performance characteristic that are relatively imperceptible to the wearer, thereby eliminating the need for the wearer to adapt to the changing performance characteristic.

Figure 21:
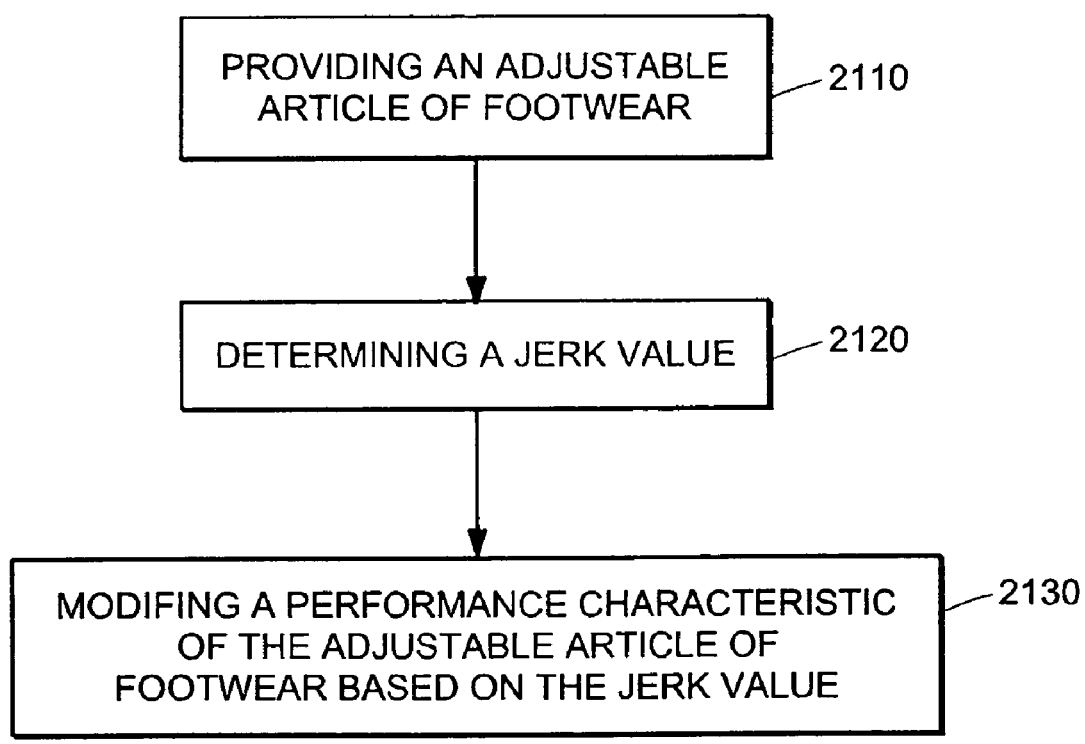
FIG. 21 is a flow chart depicting one embodiment of a method of providing comfort in an article of footwear.

FIG. 21 depicts a flow chart representing a method of providing comfort in an article of footwear. The method includes providing an adjustable article of footwear (step 2110) and determining a jerk value (step 2120). Jerk is represented as a change of acceleration over a change in time ($\Delta a/\Delta t$). The jerk value can be derived from the distance measurement, based on the changing magnetic field, over a known time period. A control system records the change in the magnetic field over time and is able to process these measurements to arrive at the jerk value. The method may further include modifying a performance characteristic of the adjustable article of footwear based on the jerk value (optional step 2130), for example, to keep the jerk value below a predetermined maximum value.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An intelligent footwear system comprising:
an article of footwear comprising a midsole, the midsole defining a cavity therein;
a system for monitoring at least one performance characteristic of the article of footwear, the monitoring system at least partially disposed in the cavity and configured for removal from the cavity, wherein the monitoring system comprises a sensor for converting the at least one performance characteristic of the article of footwear into an electrical signal and a transmitter for transmitting the electrical signal; and
a processor located remotely to the article of footwear and in communication with the monitoring system, the processor configured to receive the electrical signal and to determine at least one of velocity, acceleration, jerk, distance, and stride frequency of a wearer.

2. The intelligent footwear system of claim 1, further comprising adjusting the performance characteristic of the article of footwear.

3. The intelligent footwear system of claim 1, wherein the electrical signal is transmitted wirelessly.

4. The intelligent footwear system of claim 1, wherein the processor is disposed in a portable electronic device.

5. The intelligent footwear system of claim 4, wherein the portable electronic device includes at least one of a watch and a personal digital assistant.

6. The intelligent footwear system of claim 1, wherein the processor comprises a user input module.

7. The intelligent footwear system of claim 6, wherein the user input module allows a user to adjust the at least one performance characteristic.

8. The intelligent footwear system of claim 6, wherein the user input module comprises a display panel.

9. The intelligent footwear system of claim 1, wherein the sensor is selected from the group consisting of a pressure sensor, a force transducer, a hall effect sensor, a strain gauge, a piezoelectric element, a load cell, a proximity sensor, an optical sensor, an accelerometer, a capacitance sensor, an inductance sensor, an ultrasonic transducer and receiver, a radio frequency emitter and receiver, and a magneto-resistive element.

10. The intelligent footwear system of claim 1, wherein the monitoring system is encased in a waterproof enclosure.

11. The intelligent footwear system of claim 1, wherein the monitoring system further comprises a control system, the control system configured to modify the article of footwear in response to a signal received from the monitoring system.

12. An intelligent footwear system comprising:
an article of footwear comprising a midsole, the midsole defining a cavity therein;
a system for monitoring at least one performance characteristic of the article of footwear, the monitoring system at least partially disposed in the cavity and configured for removal from the cavity, wherein the monitoring system comprises a sensor for sensing the at least one performance characteristic and a transmitter for transmitting data corresponding to the sensed at least one performance characteristic; and
a processor located remotely to the article of footwear and in communication with the monitoring system, the processor configured to send data to and receive data from the monitoring system, wherein the at least one performance characteristic is selected from the group consisting of velocity, acceleration, jerk, distance, and stride frequency of a wearer.

13. An intelligent footwear system comprising:
an article of footwear comprising a midsole, the midsole defining a cavity therein;
a system for monitoring at least one performance characteristic of the article of footwear, the monitoring system at least partially disposed in the cavity, wherein the monitoring system comprises a sensing system for measuring the at least one performance characteristic and a control system for modifying the article of footwear without the use of a fluid bladder in response to a signal received from the sensing system, wherein the monitoring system is configured for removal from the cavity; and
a processor located remotely to the article of footwear and in communication with the monitoring system, the processor configured to send data to and receive data from the monitoring system.

14. The intelligent footwear system of claim 1, further comprising a calibration circuit for performing a calibration procedure on the monitoring system.

* * * * *